US009675249B2

(12) United States Patent
Miyazaki et al.

(10) Patent No.: US 9,675,249 B2
(45) Date of Patent: Jun. 13, 2017

(54) MAGNETIC RESONANCE IMAGING APPARATUS AND METHOD

(71) Applicant: TOSHIBA MEDICAL SYSTEMS CORPORATION, Otawara-shi (JP)

(72) Inventors: Mitsue Miyazaki, Mount Prospect, IL (US); Yuichi Yamashita, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 193 days.

(21) Appl. No.: 13/856,006

(22) Filed: Apr. 3, 2013

(65) Prior Publication Data

US 2013/0266200 A1    Oct. 10, 2013

(30) Foreign Application Priority Data

Apr. 4, 2012 (JP) ................................. 2012-085807
Mar. 6, 2013 (JP) ................................. 2013-044619

(51) Int. Cl.
*A61B 5/00* (2006.01)
*A61B 5/055* (2006.01)
(Continued)

(52) U.S. Cl.
CPC .............. *A61B 5/00* (2013.01); *A61B 5/0042* (2013.01); *A61B 5/055* (2013.01); *A61B 5/7285* (2013.01);
(Continued)

(58) Field of Classification Search
CPC ......... A61B 5/00; A61B 5/0042; A61B 5/055; A61B 5/7285; A61B 2576/026; G01R 33/5614; G01R 33/56333; G01R 33/5673
See application file for complete search history.

(56) References Cited

U.S. PATENT DOCUMENTS 7,834,623 B2* 11/2010 Iwadate ............. G01R 33/5676
                                                        324/307
7,880,464 B2*  2/2011 Yamada ............... A61B 5/0263
                                                        324/306
(Continued)

FOREIGN PATENT DOCUMENTS

CN          102028465 A    4/2011
JP        2008-067858 A    3/2008
(Continued)

OTHER PUBLICATIONS

Parienty et al., "Renal Artery Stenosis Evaluation in Chronic Kidney Disease Patients: Nonenhanced Time-Spatial Labeling Inversion-Pulse Three-dimensional MR Angiography with Regulated Breathing versus DSA", Radiology, vol. 29, Iss: 2, Available online Feb. 2011, 592-601.*
(Continued)

*Primary Examiner* — Katrina Fujita
(74) *Attorney, Agent, or Firm* — Oblon, McClelland, Maier & Neustadt, L.L.P.

(57) ABSTRACT

A magnetic resonance imaging apparatus according to an embodiment includes a collection unit and a generation unit. The collection unit collects data of an imaging area over a plurality of time phases within a certain respiratory cycle after applying a labeling pulse to a labeling area in which cerebrospinal fluid flows under a task of respiration. The generation unit generates images of a plurality of time phases depicting the cerebrospinal fluid by using the collected data.

12 Claims, 20 Drawing Sheets

(51) Int. Cl.
*G01R 33/561* (2006.01)
*G01R 33/563* (2006.01)
*G01R 33/567* (2006.01)

(52) U.S. Cl.
CPC .. *G01R 33/56333* (2013.01); *A61B 2576/026* (2013.01); *G01R 33/5614* (2013.01); *G01R 33/5673* (2013.01)

(56) References Cited

U.S. PATENT DOCUMENTS

| | | | |
|---|---|---|---|
| 9,517,033 B2* | 12/2016 | Kassai | A61B 5/055 |
| 2004/0102695 A1* | 5/2004 | Stergiopoulos et al. | 600/413 |
| 2009/0005670 A1* | 1/2009 | Ichinose | G01R 33/56366 600/410 |
| 2010/0087730 A1 | 4/2010 | Yamada et al. | |
| 2010/0219829 A1* | 9/2010 | Rehwald | G01R 33/4818 324/309 |
| 2011/0074416 A1 | 3/2011 | Yamashita et al. | |

FOREIGN PATENT DOCUMENTS

| JP | 2011-092670 A | 5/2011 |
|---|---|---|
| WO | 2004/048993 A2 | 6/2004 |

OTHER PUBLICATIONS

Saremi et al., "Optimizing Cardiac MR Imaging: Practical Remedies for Artifacts", Radiographics 2008, vol. 28, Issue 4, 1161-1187.*

Yamada et al., "Visualization of Cerebrospinal Fluid Movement with Spin Labeling at MR Imaging: Preliminary Results in Normal and Pathophysiologic Conditions", Radiology 2008, vol. 249, Issue 2, 644-652.*

Miyazaki et al., "Nonenhanced MR Angiography", Radiology 2008, vol. 248, Issue 1, 20-43.*

Chinese Office Action dated Sep. 1, 2015 in CN 201310116159.5.*

Chinese Office Action dated Oct. 10, 2014, in CN 201310116159.5.

* cited by examiner

FIG.4A
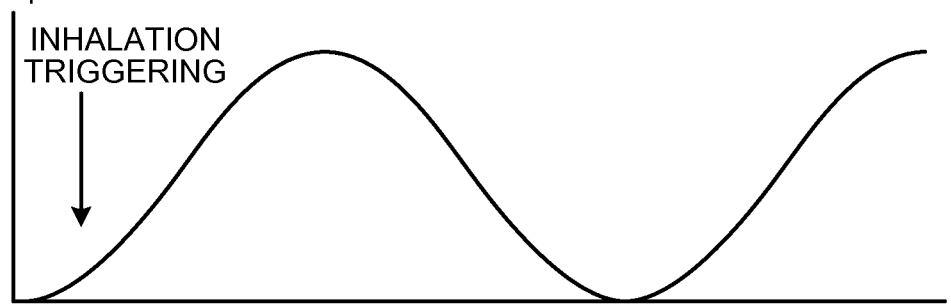
FIG.4B
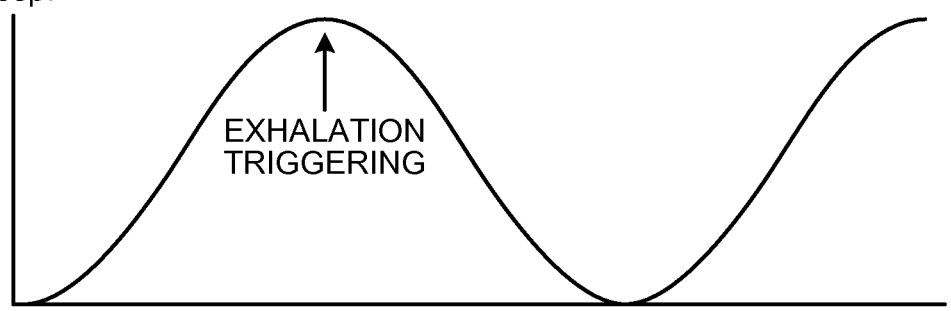
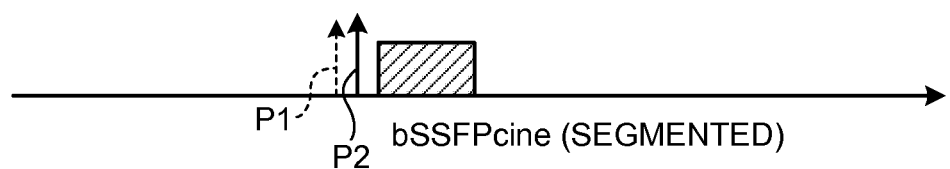

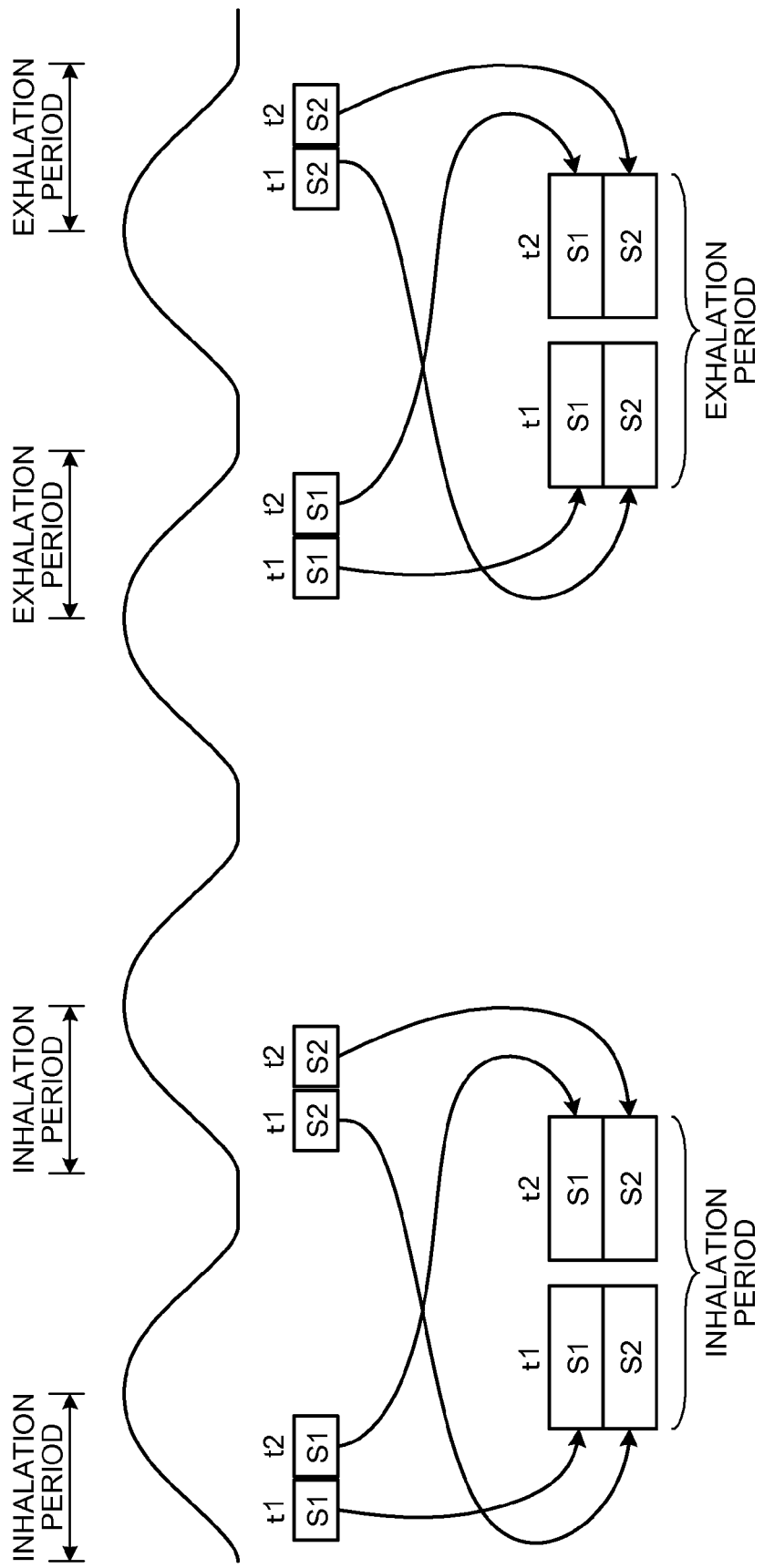

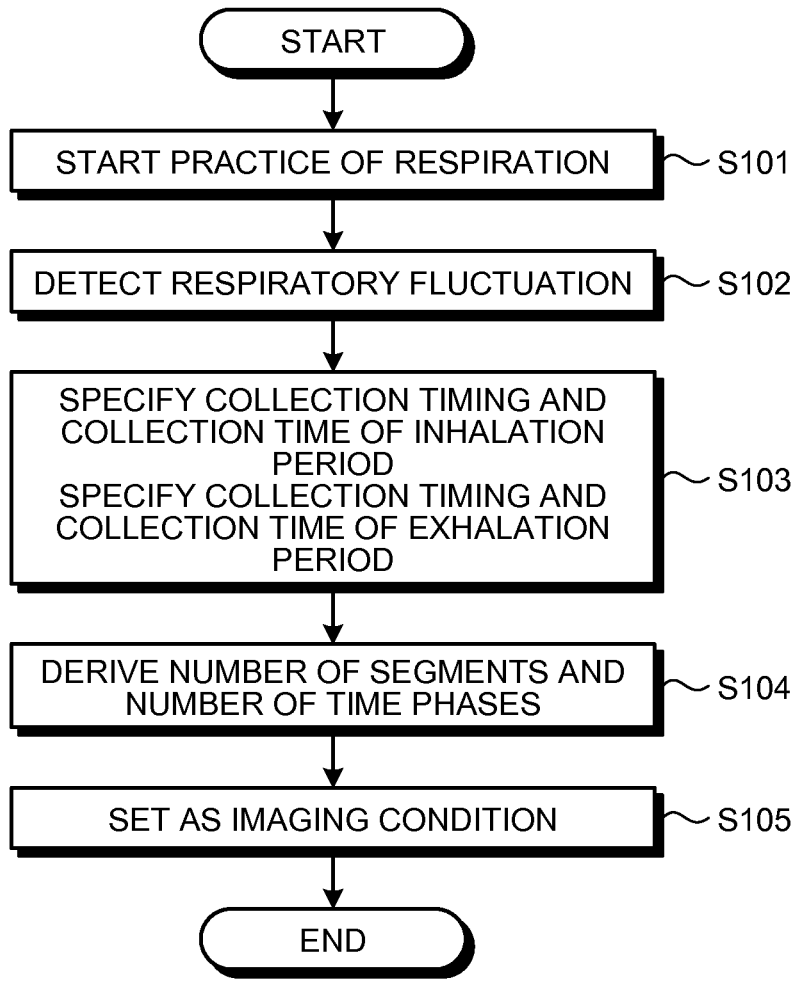

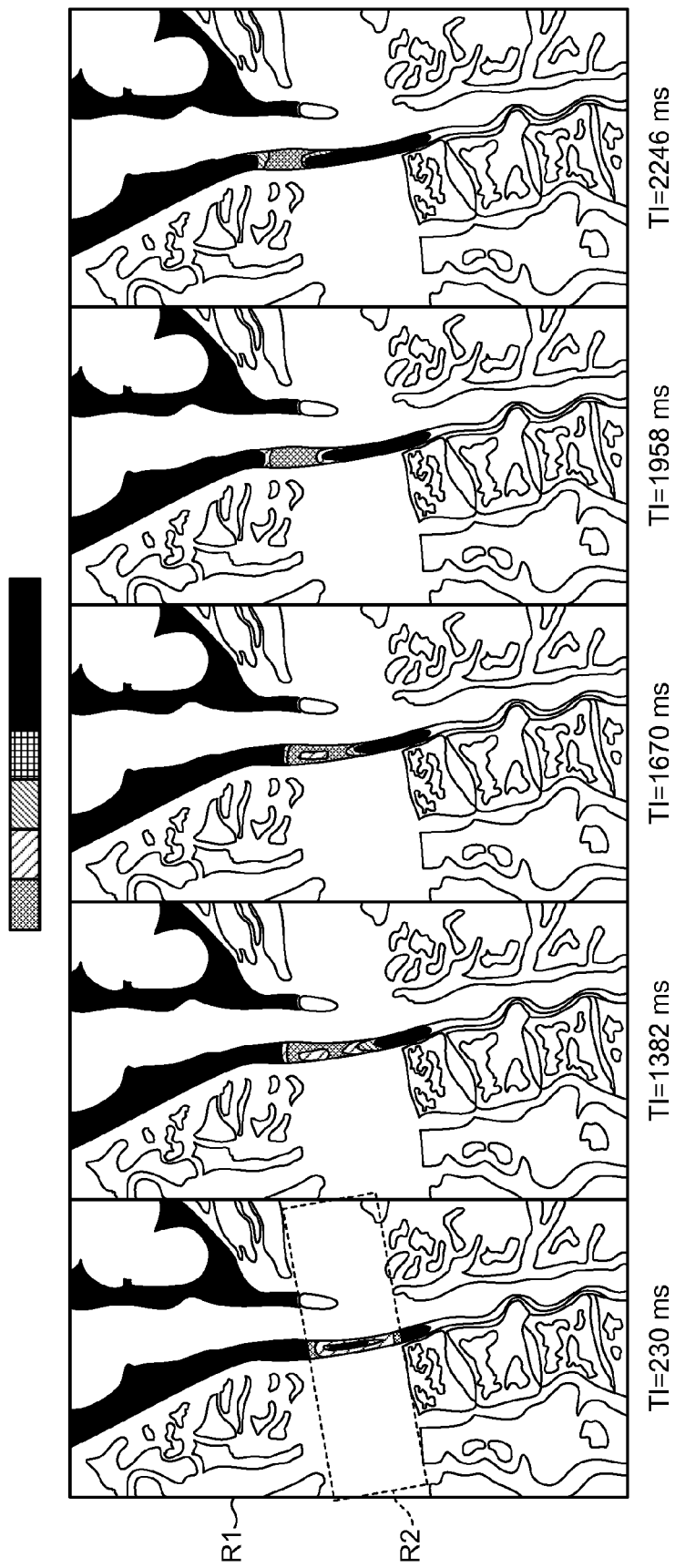

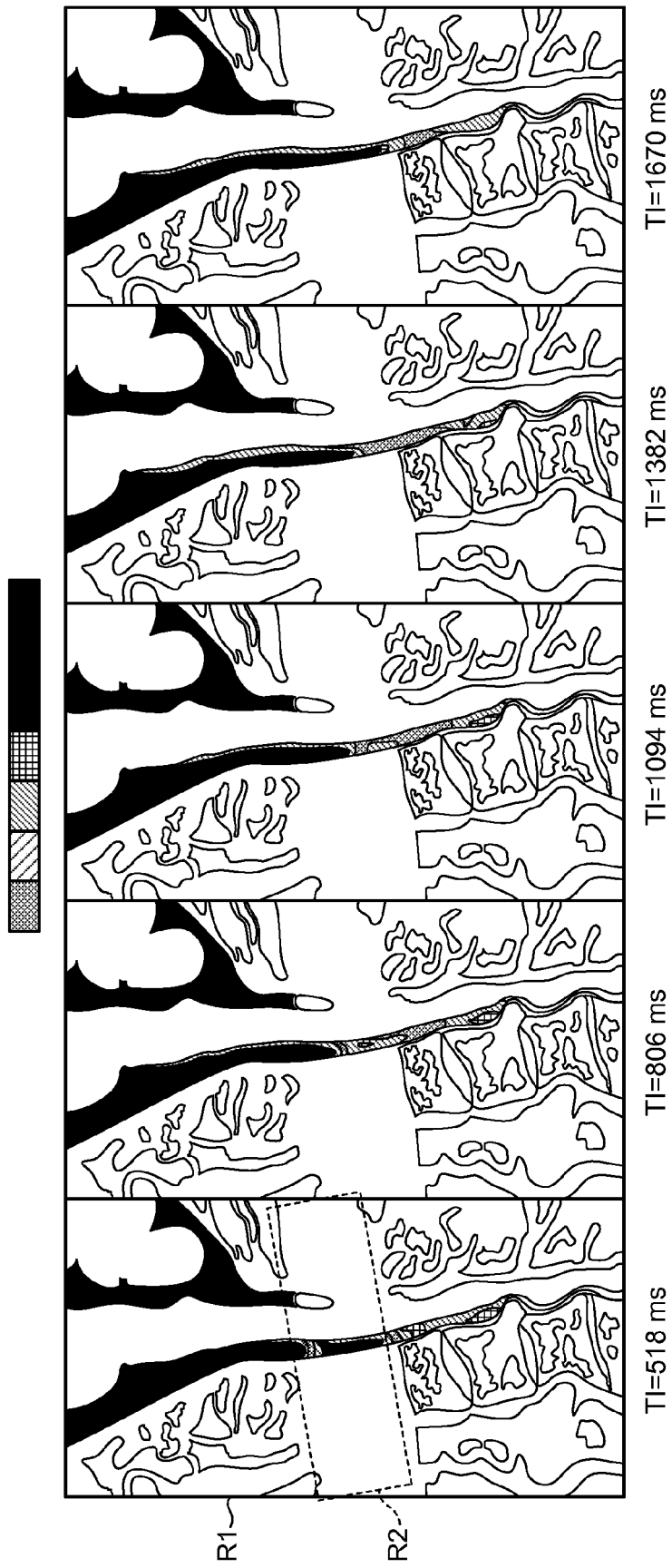

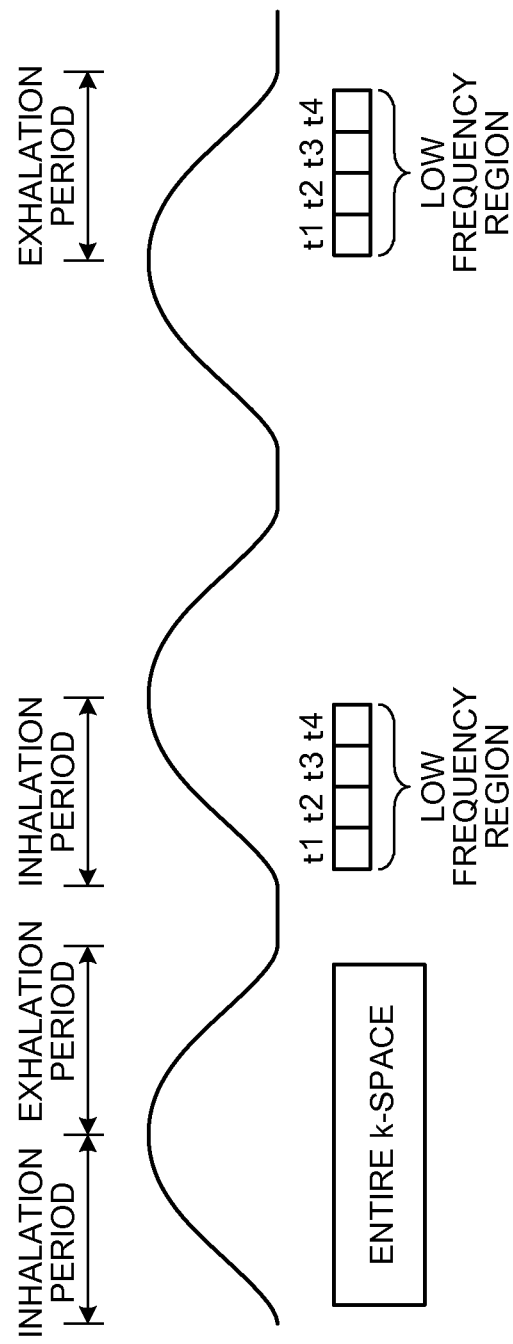

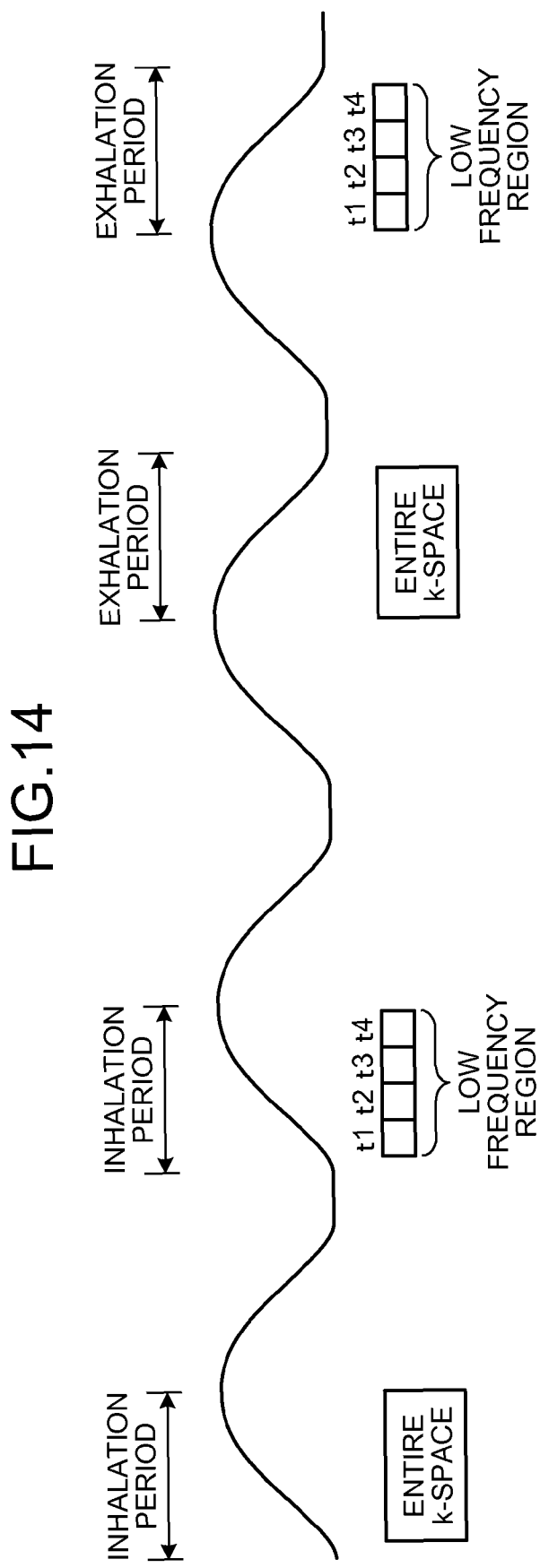

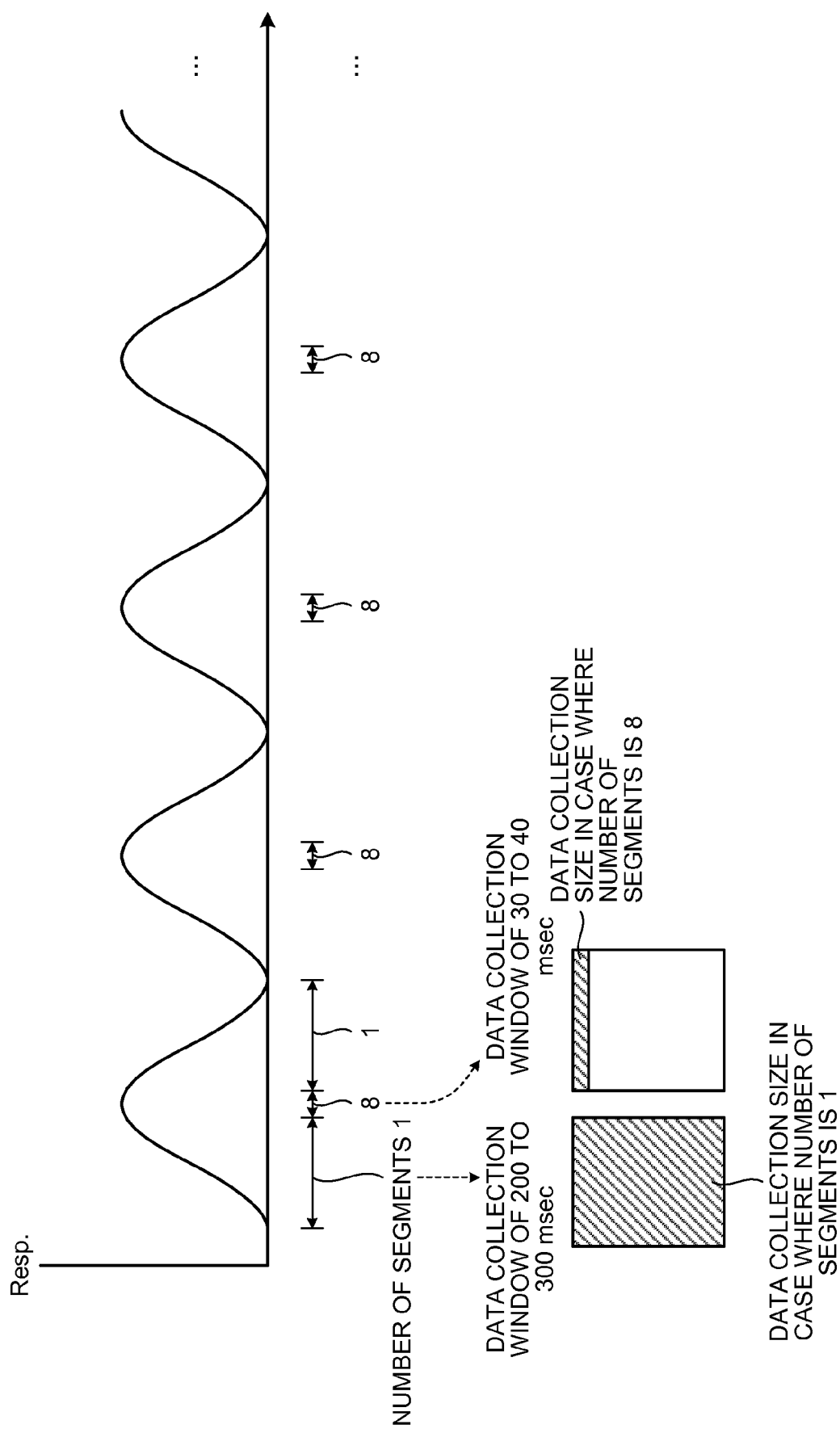

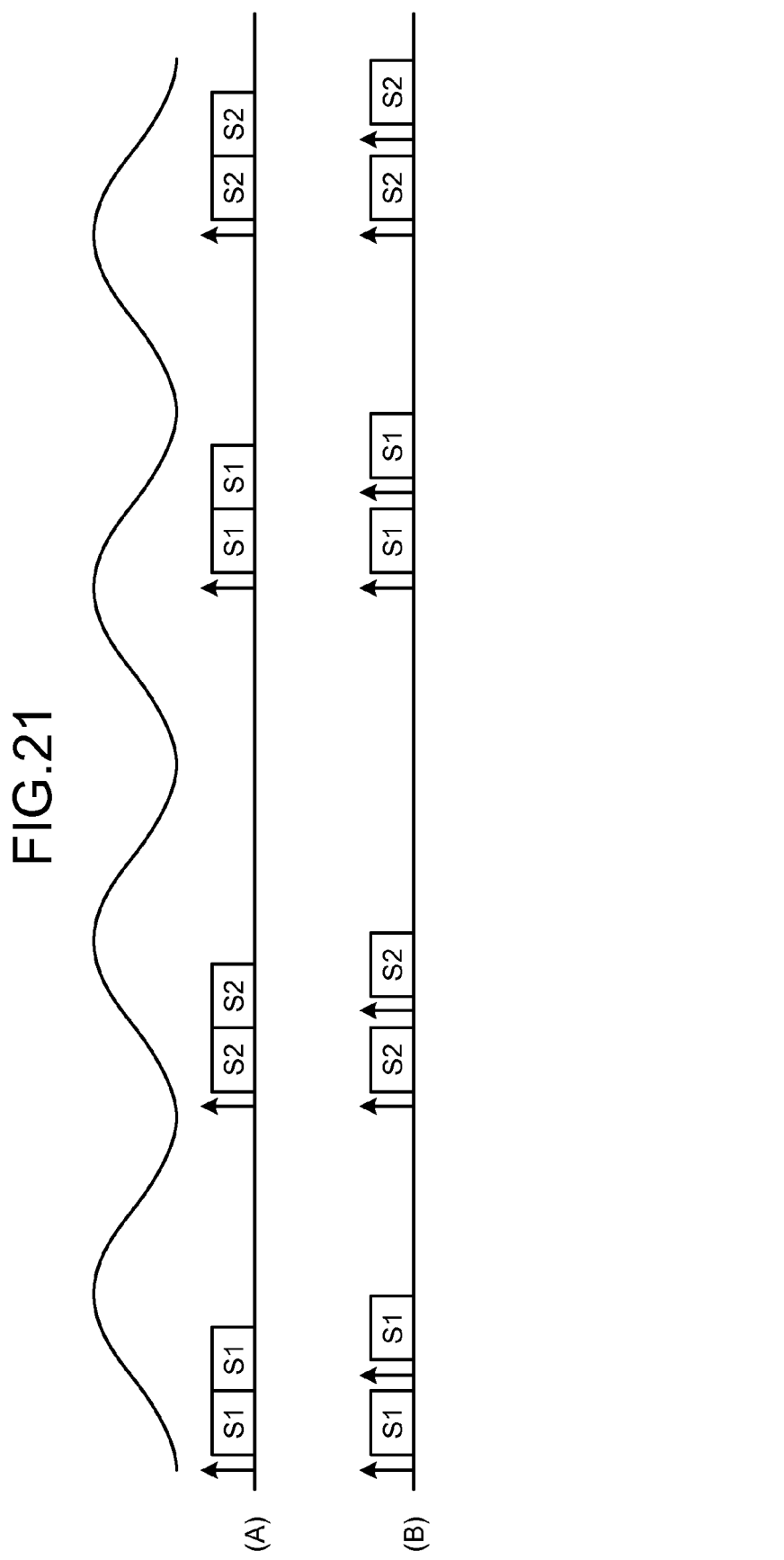

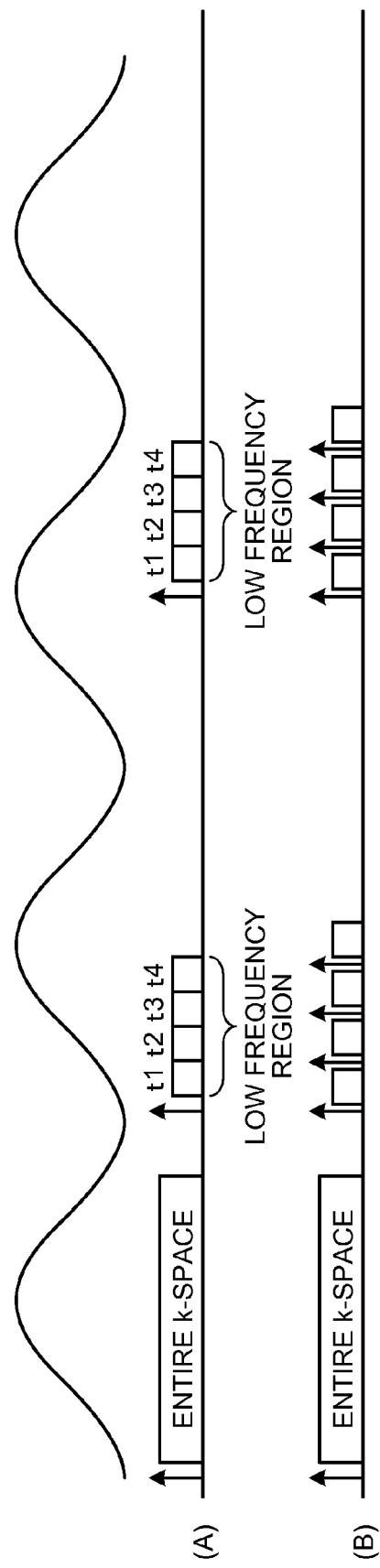

MAGNETIC RESONANCE IMAGING APPARATUS AND METHOD

CROSS-REFERENCE TO RELATED APPLICATIONS

This application is based upon and claims the benefit of priority from Japanese Patent Application No. 2012-085807, filed on Apr. 4, 2012; and Japanese Patent Application No. 2013-044619, filed on Mar. 6, 2013, the entire contents of all of which are incorporated herein by reference.

FIELD

Embodiments described herein relate generally to an apparatus and a method for magnetic resonance imaging.

BACKGROUND

In the related art, in magnetic resonance imaging, it has been known that kinetics of cerebrospinal fluid (CSF) is observed with cardiac-gated imaging. However, optimal magnetic resonance imaging is not established because the cerebrospinal fluid still remains to be elucidated.

BRIEF DESCRIPTION OF THE DRAWINGS

FIG. 4A is a diagram for explaining data collection in the first embodiment;

FIG. 4B is a diagram for explaining the data collection in the first embodiment;

FIG. 5 is a diagram for explaining the relation between the data collection and a segment in the first embodiment;

FIG. 6 is a diagram for explaining derivation of an imaging condition in the first embodiment;

FIG. 7 is a diagram for explaining CSF images in the first embodiment;

FIG. 8 is a diagram for explaining CSF images in the first embodiment;

FIG. 13 is a diagram for explaining data collection in a modification of the second embodiment;

FIG. 14 is a diagram for explaining the data collection in the modification of the second embodiment;

FIG. 20 is a diagram for explaining the data collection in the fourth embodiment;

FIG. 21 is a diagram for explaining an application of an inversion pulse in a fifth embodiment; and FIG. 22 is a diagram for explaining the application of the inversion pulse in the fifth embodiment.

DETAILED DESCRIPTION

A magnetic resonance imaging apparatus according to an embodiment includes a collection unit and a generation unit. The collection unit collects data of an imaging area over a plurality of time phases within a certain respiratory cycle after applying a labeling pulse to a labeling area in which cerebrospinal fluid flows under a task of respiration. The generation unit generates images of a plurality of time phases depicting the cerebrospinal fluid by using the collected data.

First Embodiment

Figure 1:
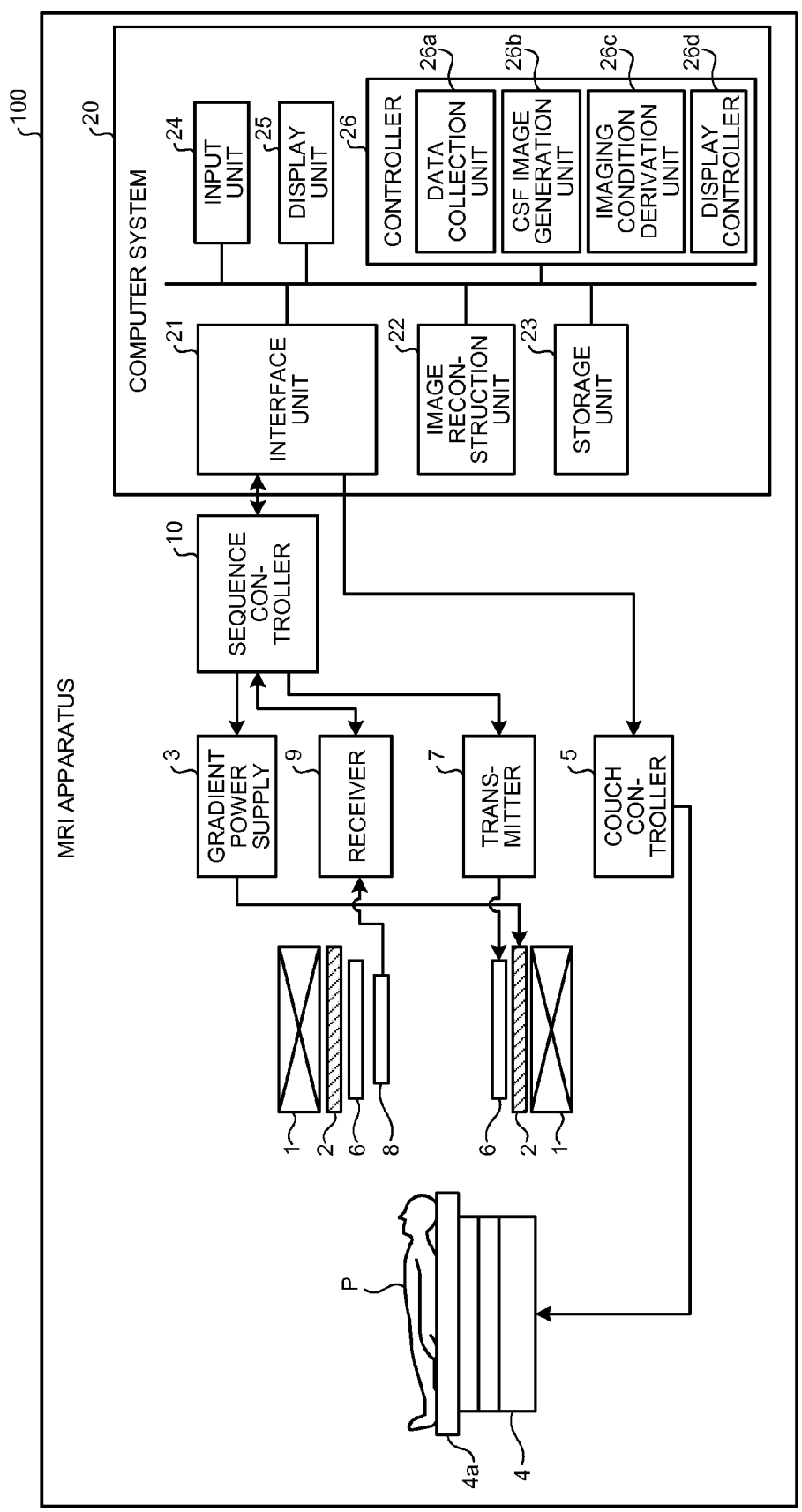
FIG. 1 is a block diagram illustrating a configuration of a magnetic resonance imaging (MRI) apparatus according to a first embodiment.

Embodiments of a magnetic resonance imaging apparatus (MRI apparatus) and a method thereof will be described below. FIG. 1 is a block diagram illustrating a configuration of this MRI apparatus 100 according to a first embodiment. The MRI apparatus 100 does not include a subject P.

A static magnetic field magnet 1 is formed in a hollow cylindrical shape and generates a uniform static magnetic field in the internal space thereof. The static magnetic field magnet 1 is, for example, a permanent magnet or a superconducting magnet. A gradient coil 2 is formed in a hollow cylindrical shape and generates a gradient magnetic field in the internal space thereof. Specifically, the gradient coil 2 is arranged inside the static magnetic field magnet 1, is supplied with electrical current from a gradient power supply 3, and generates the gradient magnetic field. The gradient power supply 3 supplies electrical current to the gradient coil 2 according to a control signal transmitted from a sequence controller 10.

A couch 4 includes a couchtop 4a on which the subject P is mounted, and inserts the couchtop 4a, in a state where the subject P is mounted thereon, into the cavity of the gradient coil 2 serving as a port for imaging. Generally, the couch 4 is installed such that the longitudinal direction thereof is parallel to the central axis of the static magnetic field magnet 1. A couch controller 5 drives the couch 4 to move the couchtop 4a in the longitudinal direction and the vertical direction.

A transmission coil 6 generates a high frequency magnetic field. Specifically, the transmission coil 6 is arranged inside the gradient coil 2, is supplied with an RF pulse from a transmitter 7, and generates the high frequency magnetic field. The transmitter 7 transmits the RF pulse corresponding to the Larmor frequency to the transmission coil 6 according to a control signal transmitted from the sequence controller 10.

A reception coil 8 receives a magnetic resonance signal (hereinafter, referred to as magnetic resonance (MR) signal). Specifically, the reception coil 8 is arranged inside the gradient coil 2 and receives the MR signal radiated from the subject P caused by an influence of the high frequency magnetic field. The reception coil 8 outputs the received MR signal to a receiver 9.

The receiver 9 generates MR signal data on the basis of the MR signal output from the reception coil 8 according to a control signal transmitted from the sequence controller 10. Specifically, the receiver 9 generates the MR signal data by digital conversion of the MR signal output from the reception coil 8, and transmits the generated MR signal data to a computer system 20 via the sequence controller 10. The receiver 9 may be provided to a gantry including the static magnetic field magnet 1 and the gradient coil 2.

The sequence controller 10 controls the gradient power supply 3, the transmitter 7, and the receiver 9. Specifically, the sequence controller 10 transmits the control signals based on pulse sequence execution data transmitted from the computer system 20, to the gradient power supply 3, the transmitter 7, and the receiver 9.

The computer system 20 includes an interface unit 21, an image reconstruction unit 22, a storage unit 23, an input unit 24, a display unit 25, and a controller 26. The interface unit 21 is connected to the sequence controller 10 and controls input/output of data transmitted/received between the sequence controller 10 and the computer system 20. The image reconstruction unit 22 reconstructs image data from the MR signal data transmitted from the sequence controller 10, and stores the reconstructed image data in the storage unit 23.

The storage unit 23 stores the image data stored by the image reconstruction unit 22 and other data used in the MRI apparatus 100. For example, the storage unit 23 is a semiconductor memory element such as a random access memory (RAM) or a flash memory, a hard disc, or an optical disc.

The input unit 24 receives various instructions and instructions for imaging from an operator. For example, the input unit 24 is a mouse and a keyboard. The display unit 25 displays an edit screen of imaging conditions and images. For example, the display unit 25 is a liquid crystal display.

The controller 26 controls the MRI apparatus 100 as a whole by controlling the components described above. For example, upon accepting the imaging conditions edited by the operator, the controller 26 generates pulse sequence execution data based on the accepted imaging conditions, and transmits the generated pulse sequence execution data to the sequence controller 10. For example, the controller 26 is an integrated circuit such as an application specific integrated circuit (ASIC) or a field programmable gate array (FPGA), or an electronic circuit such as a central processing unit (CPU) or a micro processing unit (MPU).

As illustrated in FIG. 1, the controller 26 according to the first embodiment includes a data collection unit 26a, a CSF image generation unit 26b, an imaging condition derivation unit 26c, and a display controller 26d. The data collection unit 26a cooperates with the sequence controller 10 and the like to apply a labeling pulse (tagging pulse) to a labeling area (tagging area) in which cerebrospinal fluid (CSF) flows under a task of respiration, thereby collecting data of an imaging area over a plurality of time phases within one respiratory cycle. The CSF image generation unit 26b cooperates with the image reconstruction unit 22 and the like to generate CSF images of a plurality of time phases by using the data collected by the data collection unit 26a. The imaging condition derivation unit 26c specifies a period in which respiratory fluctuation is large based on the waveform of the respiratory fluctuation of a subject, and derives imaging conditions for collecting data (for example, the number of segments and the number of time phases) according to the specified period. The display controller 26d displays, in parallel or as a moving image, the CSF images of the time phases generated by the CSF image generation unit 26b on the display unit 25.

The data collection unit 26a according to the first embodiment collects data by using the arterial spin labeling (ASL) method or the time spatial labeling inversion pulse (Time-SLIP) method, and by using a pulse sequence of the gradient echo (GRE) group. First, the following will describe the pulse sequence used by the data collection unit 26a according to the first embodiment.

Figure 2:
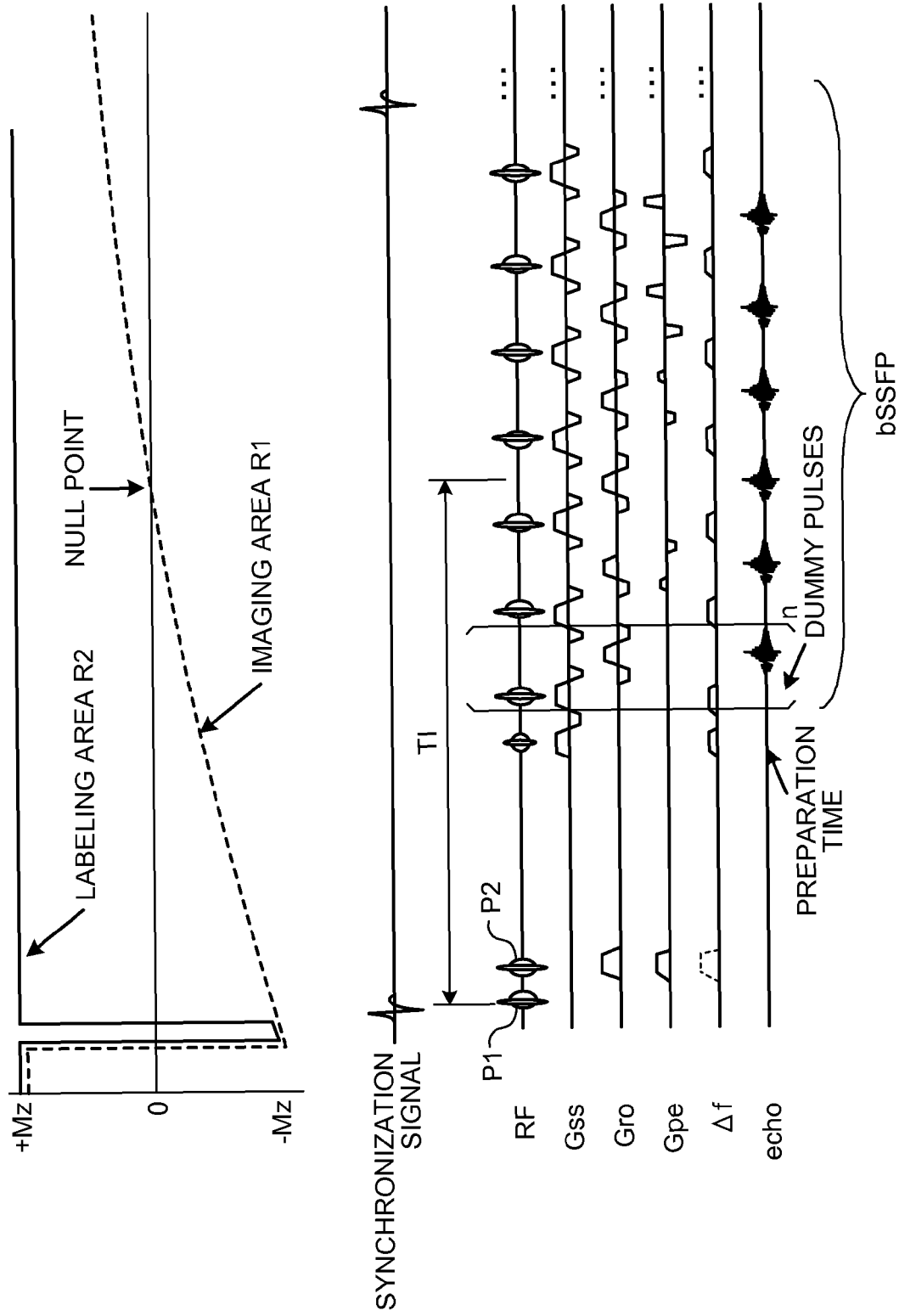
FIG. 2 is a diagram for explaining a pulse sequence in the first embodiment.
Figure 3A:
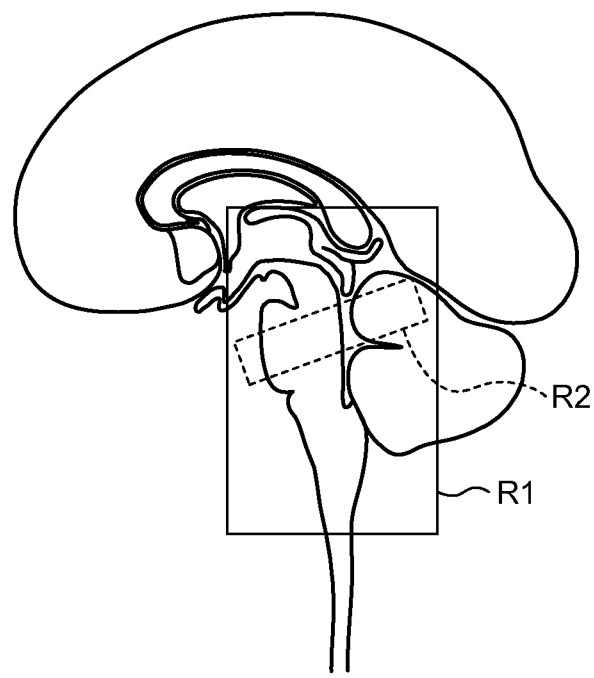
FIG. 3A is a diagram for explaining the pulse sequence in the first embodiment.
Figure 3B:
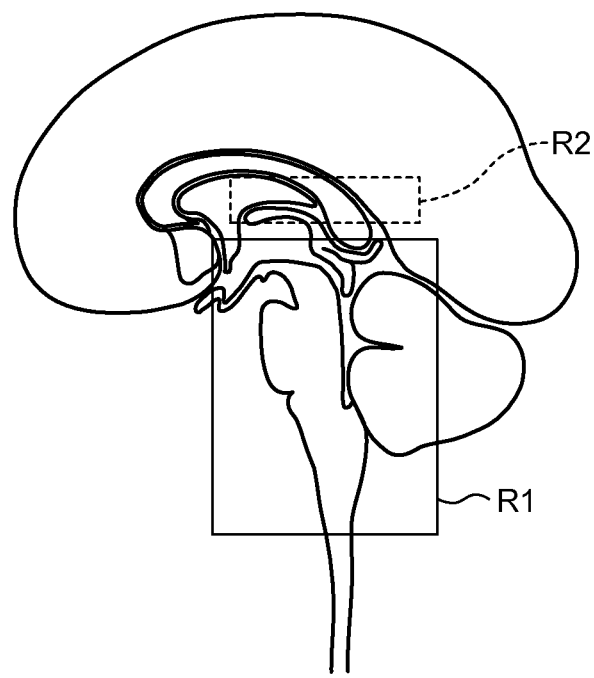
FIG. 3B is a diagram for explaining the pulse sequence in the first embodiment.

FIG. 2, FIG. 3A, and FIG. 3B are diagrams for explaining the pulse sequence in the first embodiment. The ASL method is a method for visualizing fluid such as blood or CSF, without a contrast medium, by magnetically labeling the fluid itself with the RF pulse and using the labeled fluid as a tracer. The Time-SLIP method is a method for visualizing the fluid that flows from or into the imaging area by labeling the fluid in the labeling area independent of the imaging area and then increasing or decreasing a signal value of the fluid that flows out from or into the imaging area.

The Time-SLIP method includes flow-out and flow-in. In the case of flow-out, a labeling area R2 in which the CSF flows is set within an imaging area R1 as illustrated in FIG. 3A, for example. The data collection unit 26a applies a non-selective (area-non selecting) inversion pulse p1 to the entire imaging area R1, and subsequently, applies a selective (area-selecting) inversion pulse p2 to the labeling area R2 in the imaging area R1. In this case, first, the non-selective inversion pulse p1 is applied to the entire imaging area R1, so that the longitudinal magnetization components of signals in the entire imaging area R1 are inverted as illustrated with a dotted line in FIG. 2. Subsequently, the selective inversion pulse p2 is applied to the labeling area R2 in the imaging area R1, so that the longitudinal magnetization component only of a signal in the labeling area R2 is inverted again as illustrated with a solid line in FIG. 2. Thus, after a particular time elapses, a signal other than the labeled signal is recovered and the longitudinal magnetization component thereof becomes zero (Null Point). Consequently, when the signal of the labeled CSF flows out from the labeling area R2 and enters the imaging area R1, the signal value thereof is visualized as a high signal value. The application of the non-selective inversion pulse p1 may be omitted.

In other words, the non-selective inversion pulse p1 and the selective inversion pulse p2 are made as inversion recovery (IR) pulses, and the time between the application of the non-selective inversion pulse p1 and the application of the selective inversion pulse p2 is made extremely short relative to the moving speed of the CSF. This allows the longitudinal magnetization of spin of the CSF flowing out from the labeling area R2 to be returned to nearly an initial state while the longitudinal magnetization of spin in the imaging area R1 except the labeling area R2 is in an inverted state. Thus, the CSF flowing out from the labeling area R2 is depicted as a high signal relative to the background tissue. In a case where the application of the non-selective inversion pulse p1 is omitted, the CSF flowing out from the labeling area R2 is depicted as a low signal relative to the background tissue.

In contrast, in the case of flow-in, the labeling area R2 in which the CSF flows is set outside the imaging area R1 as illustrated in FIG. 3B, for example. The data collection unit 26a does not apply the non-selective inversion pulse p1 but applies the selective inversion pulse p2 to the labeling area R2 outside the imaging area R1. In this case, the longitudinal magnetization component only of the signal in the labeling area R2 is inverted. Consequently, if the labeled signal flows into the imaging area R1 after a particular time elapses, the signal value thereof is visualized as a low signal value.

The data collection unit 26a may apply the non-selective inversion pulse p1. For example, the data collection unit 26a may apply the selective inversion pulse p2 to the labeling area R2 even number of times (for example, twice). In this case, the longitudinal magnetization of spin of the CSF flowing out from the labeling area R2 is returned to nearly the initial state while the longitudinal magnetization of spin in the imaging area R1 is in the inverted state. Thus, the CSF flowing out from the labeling area R2 is depicted as a high signal relative to the background tissue.

Flow-out and flow-in are not limited to the definitions described above and may be called with the opposite names or other names depending on a manner of definition. Settings of the imaging area and the labeling area may be optionally changed according to the purpose of imaging.

The position of the labeling area and the number of the labeling areas may be optionally changed. As a pulse for labeling, an inversion recovery (IR) pulse, saturation (SAT) pulse, a spatial modulation of magnetization (SPAMM) pulse, a DANTE pulse, or the like may be used. The SAT pulse is a pulse that saturates the longitudinal magnetization component by causing the magnetization vector of the labeling area to be inclined by 90°. The SPAMM pulse and the DANTE pulse each form an area saturated with a desired pattern such as a stripe pattern, a grid pattern, or a radial pattern by adjusting the gradient magnetic field.

As illustrated in FIG. 2, the data collection unit 26a according to the first embodiment collects data by applying the non-selective inversion pulse p1 and the selective inversion pulse p2 and subsequently using a pulse sequence of the balanced steady-state free precession (bSSFP) of the GRE group. The pulse sequence is not limited to a pulse sequence of the bSSFP, and any pulse sequence of the GRE group may be used. For example, the fast field echo (FFE) may also be used.

FIG. 4A and FIG. 4B are diagrams for explaining data collection in the first embodiment. In FIG. 4A and FIG. 4B, "Resp." is an abbreviation of respiration, and waveforms illustrated in FIG. 4A and FIG. 4B indicate respiratory fluctuation waveforms (for example, fluctuation waveforms of a diaphragm) of a subject given a task of respiration. For example, during a period when the subject breathes in (inhalation, hereinafter referred to as inhalation period or period of inhalation as appropriate), the respiratory fluctuation waveform rises along a gentle curve. During a period when the subject breathes out (exhalation, hereinafter referred to as exhalation period or period of exhalation as appropriate), the respiratory fluctuation waveform goes down along a gentle curve. Although the respiratory fluctuation waveform is slightly fluctuated in practice because of an influence of a heartbeat, the degree of change due to the fluctuation is negligible.

As illustrated in FIG. 4A, the data collection unit 26a according to the first embodiment applies the non-selective inversion pulse p1 and the selective inversion pulse p2 to the labeling area with the starting of an inhalation period as a trigger (Inhalation triggering), and subsequently, collects data of the imaging area within one respiratory cycle over a plurality of time phases by using the pulse sequence of the bSSFP. Similarly, as illustrated in FIG. 4B, the data collection unit 26a applies the non-selective inversion pulse p1 and the selective inversion pulse p2 to the labeling area with the starting of an exhalation period as a trigger (exhalation triggering), and subsequently, collects data of the imaging area within one respiratory cycle over a plurality of time phases by using the pulse sequence of the bSSFP.

In FIG. 4A and FIG. 4B, "cine" indicates collection of data of the imaging area over a plurality of time phases, and "segmented" indicates collection of data for one segment among k-space data divided into a plurality of segments (or part of the k-space data divided into a plurality of segments) within one respiratory cycle, as described later. Although an example of the pulse sequence in the case of flow-out is described in the first embodiment, this description may also be applied to the pulse sequence in the case of flow-in.

In the above description, the data collection is triggered by the starting of the inhalation period or the exhalation period. This means that the data collection unit 26a collects data in the imaging area in a period in which the respiratory fluctuation is large in one respiratory cycle. In other words, for example, the data collection unit 26a according to the first embodiment collects data in an initial period in which the subject starts to breathe in in a breathe-in period, and collects data in an initial period in which the subject starts to breathe out in a breathe-out period.

For example, the data collection unit 26a receives a signal of a voice instruction given to the subject or an instruction displayed on the display unit 25 (for example, "please breathe in" or "please breathe out") as an input, and applies the inversion pulse in synchronization with the signal as a trigger. For example, the data collection unit 26a detects the respiratory fluctuation of the subject by a method of detecting fluctuation of the diaphragm of the subject or a method of detecting fluctuation of a marker fitted to the subject, and applies the inversion pulse in synchronization with the detected respiratory fluctuation. However, in consideration of a case where the respiratory cycle is 8 seconds for example and a period in which contrast can be provided to the image by labeling is 4 seconds for example, the latter method of applying the inversion pulse in synchronization with the detected respiratory fluctuation may put the application behind an appropriate timing. Thus, the former method of applying the inversion pulse with the signal such as a voice instruction as a trigger is preferable.

The data collection unit 26a according to the first embodiment collects data for one segment among the data of the imaging area divided into a plurality of segments over a plurality of time phases within one respiratory cycle. The CSF image generation unit 26b according to the first embodiment generates the CSF images of the time phases by combining pieces of data of the respective segments collected by the data collection unit 26a in each of the respiratory cycles.

FIG. 5 is a diagram for explaining the relation between the data collection and the segment in the first embodiment. For example, it is assumed that the data of the k-space is divided into two segments in the first embodiment. In addition, it is assumed that the data over two time phases is collected within one respiratory cycle in the first embodiment. In this case, for example, as illustrated in FIG. 5, the data collection unit 26a according to the first embodiment collects data of two time phases (that is, a time phase t1 and a time phase t2) for a segment 1 (S1) in an initial inhalation period in which the respiratory fluctuation is large. Subsequently, the data collection unit 26a collects data of the two time phases (that is, the time phase t1 and the time phase t2) for a segment 2

(S2) in an initial inhalation period in which the respiratory fluctuation is large. The data collection unit 26a collects data of two time phases (that is, a time phase t1 and a time phase t2) for the segment 1 (S1) in an initial exhalation period in which the respiratory fluctuation is large. Subsequently, the data collection unit 26a collects data of the two time phases (that is, the time phase t1 and the time phase t2) for the segment 2 (S2) in an initial exhalation period in which the respiratory fluctuation is large. The CSF image generation unit 26b, as illustrated in FIG. 5, generates an image for each of the time phases by combining and reconstructing these pieces of data as one piece of data of the k-space for each of the time phases.

Although FIG. 5 illustrates an example in which the data is collected in the order of "inhalation period"→"inhalation period"→"exhalation period"→"exhalation period", the embodiment is not limited thereto. For example, the order may be optionally changed as "inhalation period"→"exhalation period"→"inhalation period"→"exhalation period", or "exhalation period"→"exhalation period"→"inhalation period"→"inhalation period". However, in light of the recovery time of the labeled longitudinal magnetization component, it is preferable that a series of "inhalation period" and a series of "exhalation period" are performed separately in different respiratory cycles instead of being sequentially performed in one respiratory cycle.

The following will describe how the imaging conditions such as the number of segments and the number of time phases are set in the first embodiment. In the first embodiment, the imaging condition derivation unit 26c specifies the period in which the respiratory fluctuation is large based on the waveform of the respiratory fluctuation of the subject, and derives the number of segments and the number of time phases according to the specified period. The data collection unit 26a sets the number of segments and the number of time phases derived by the imaging condition derivation unit 26c to the pulse sequence and collects data. The respiratory cycle is usually different from subject to subject. According to the first embodiment, the number of segments and the number of time phases appropriate for each subject may be set to the pulse sequence.

FIG. 6 is a diagram for explaining derivation of the imaging condition in the first embodiment. As illustrated in FIG. 6, it is assumed in the first embodiment that the subject is caused to practice respiration before a diagnostic medical image is imaged. That is, the imaging condition derivation unit 26c starts the practice of respiration by giving a voice instruction such as "please breathe in" or "please breathe out" to the subject (step S101).

Next, the imaging condition derivation unit 26c detects the waveform of the respiratory fluctuation of the subject during the practicing period (step S102). The detection may be achieved by a known technique. For example, the imaging condition derivation unit 26c detects the waveform of the respiratory fluctuation of the subject by a method of detecting the fluctuation of the diaphragm of the subject or a method of detecting the fluctuation of a marker fitted to the subject.

Subsequently, the imaging condition derivation unit 26c analyzes the detected waveform of the respiratory fluctuation to specify the period in which the respiratory fluctuation is large from the waveform and length of the inhalation period and the waveform and length of the exhalation period, and specifies appropriate collection timing and collection time of the inhalation period and appropriate collection timing and collection time of the exhalation period (step S103). The collection timing includes timing for applying the inversion pulse (for example, a delay time from the inputting of a voice signal) and start timing for collecting the data thereafter.

The imaging condition derivation unit 26c derives the appropriate number of segments and the appropriate number of time phases by using the collection time and the like specified at step S103 (step S104). For example, an increase in the number of segments decreases data volume for one segment, thereby increasing the number of time phases that can be collected within one respiratory cycle to enhance time resolution. For example, a reduction of spatial resolution also decreases the data volume for one segment, thereby increasing the number of time phases that can be collected within one respiratory cycle to enhance the time resolution. As described herein, the collection time, the number of segments and the number of time phases, and the time resolution or the spatial resolution are correlated with each other, so that imaging conditions to be prioritized from which the other imaging conditions are derived depend on the purpose of imaging and the like, for example. The imaging condition derivation unit 26c, for example, stores formulae including these elements as variables in advance, and calculates the number of segments and the number of time phases appropriate for an individual subject while adjusting required time resolution and spatial resolution.

In this manner, the imaging condition derivation unit 26c sets the number of segments and the number of time phases derived at step S104 as the imaging conditions (step S105).

As described above, the display controller 26d according to the first embodiment displays, in parallel or as a moving image, the CSF images of the time phases generated by the CSF image generation unit 26b on the display unit 25.

Figure 9:
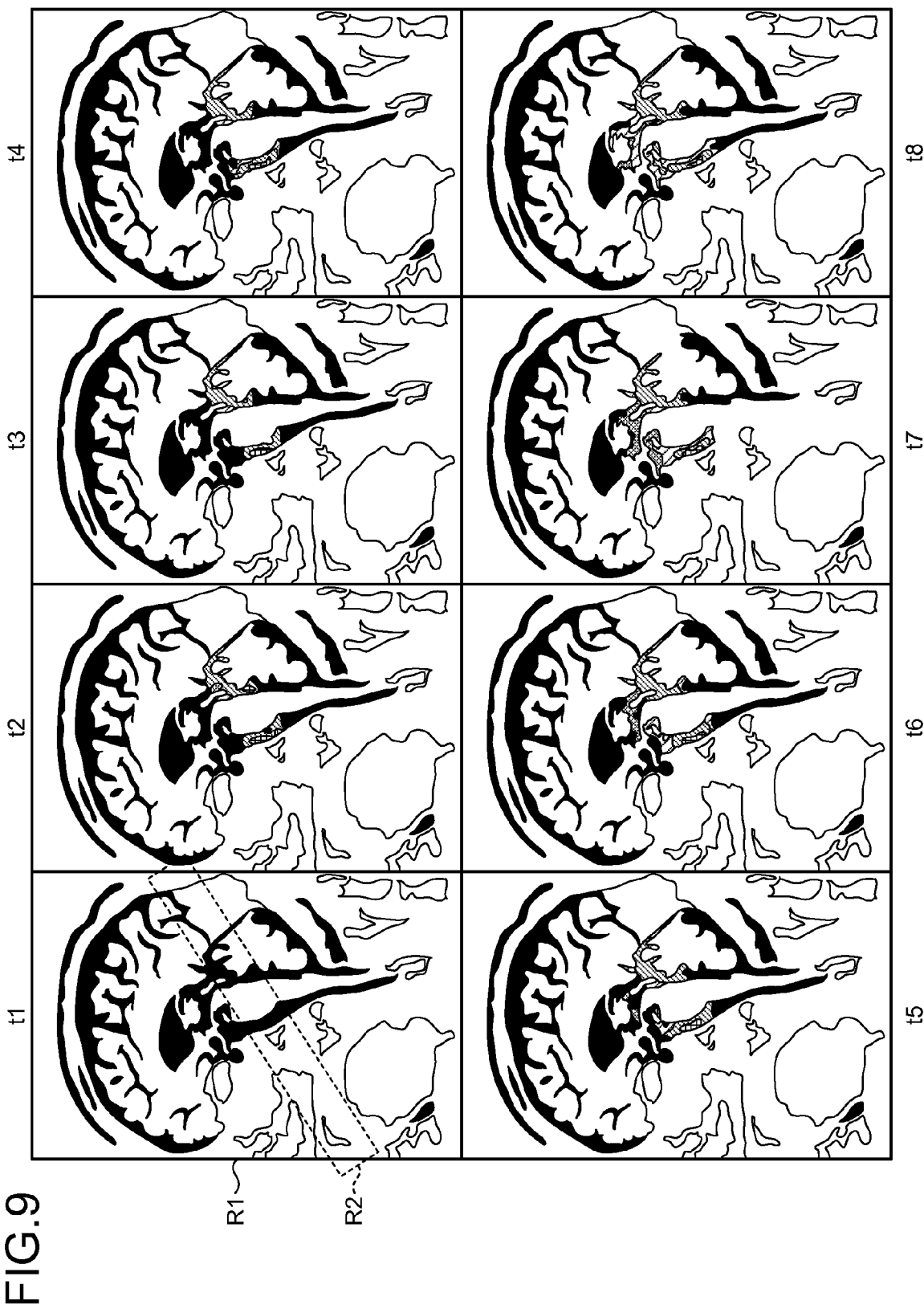
FIG. 9 is a diagram for explaining CSF images in the first embodiment.
Figure 10:
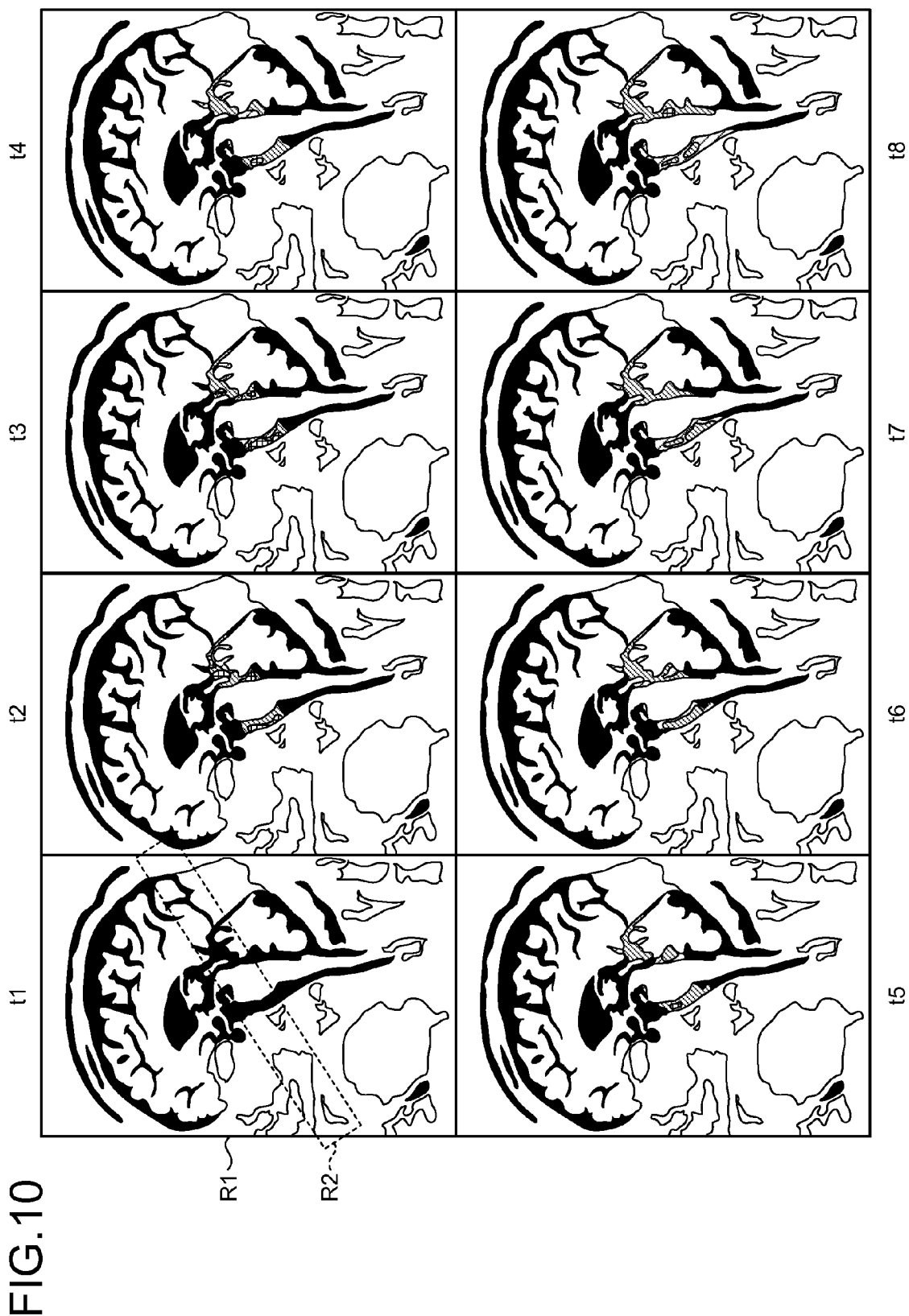
FIG. 10 is a diagram for explaining CSF images in the first embodiment.

FIG. 7 to FIG. 10 are diagrams for explaining the CSF images in the first embodiment. Although the number of time phases is assumed to be two in the above description, FIG. 7 to FIG. 10 illustrate an example of a case where CSF images are collected over a larger number of time phases. For example, as illustrated in FIG. 7, the display controller 26d displays, as a moving image, CSF images of a plurality of time phases collected in an inhalation period by applying an inversion pulse to the labeling area R2 through which the CSF flows. Similarly, as illustrated in FIG. 8, the display controller 26d displays, as a moving image, CSF images of a plurality of time phases collected in an exhalation period by applying an inversion pulse to the labeling area R2 through which the CSF flows. Similarly, although the imaging area is slightly different from that in FIG. 7 and FIG. 8, as illustrated in FIG. 9, the display controller 26d displays, as a moving image, CSF images of a plurality of time phases collected in an inhalation period by applying an inversion pulse to the labeling area R2 in which the CSF flows. Similarly, as illustrated in FIG. 10, the display controller 26d displays, as a moving image, CSF images of a plurality of time phases collected in an exhalation period by applying an inversion pulse to the labeling area R2 in which the CSF flows.

In FIG. 7 to FIG. 10, portions represented by various patterns correspond to portions representing signals of the labeled CSF, and kinetics of the CSF is visualized by displaying the CSF images of a plurality of time phases as a moving image. The display controller 26d may display the portions by color codes with colors allocated to respective patterns, instead of the above-described patterns. The display controller 26d may display these CSF images on one screen side by side. The display controller 26d may display the CSF time-series images of the inhalation period and the CSF time-series images of the exhalation period side by side, or the display controller 26d may display the CSF moving images of the inhalation period and the CSF moving images of the exhalation period side by side.

In this manner, for example, the CSF image generation unit 26b generates CSF images of a plurality of time phases collected in an initial period in which the respiratory fluctuation is large in a period of inhalation, from the data collected by the data collection unit 26a. The display controller 26d displays the CSF images of the time phases as a moving image. As can be seen from FIG. 7 or FIG. 9, it is observed that the signal of the CSF tends to move upward in the period of inhalation.

For example, the CSF image generation unit 26b generates CSF images of a plurality of time phases collected in an initial period in which the respiratory fluctuation is large in a period of exhalation, from the data collected by the data collection unit 26a. The display controller 26d displays the CSF images of the time phases as a moving image. As can be seen from FIG. 8 or FIG. 10, it is observed that the signal of the CSF tends to move downward in the period of exhalation.

The CSF image generation unit 26b does not necessarily have to generate the CSF image by using all pieces of data collected by the data collection unit 26a. The CSF image generation unit 26b may selectively generate the image by using only a piece of data corresponding to a desired period among the data collected by the data collection unit 26a. The same applies to the other embodiments below.

For example, the CSF image generation unit 26b may generate only the CSF images of either the period of inhalation or the period of exhalation. Alternatively, for example, in a case of generating the CSF image in the period of inhalation or exhalation, the CSF image generation unit 26b may omit the collected data as appropriate, for example, by omitting the data of previous and next time phases or thinning out the data of an intermediate time phase. Similarly, regardless of whether the CSF image is generated by the CSF image generation unit 26b, the display controller 26d may display only the CSF images of either inhalation or exhalation as a moving image, or may display the CSF images with the data of some time phases omitted.

As described above, the kinetics of the CSF may be visualized according to the first embodiment.

Second Embodiment

Next, a second embodiment will be described. Although the first embodiment describes an example in which data of the k-space is simply divided into two segments in a phase encoding direction, the embodiment is not limited thereto. The MRI apparatus 100 according to the second embodiment may have the same configuration as that of the MRI apparatus 100 according to the first embodiment unless otherwise specifically noted.

Figure 11:
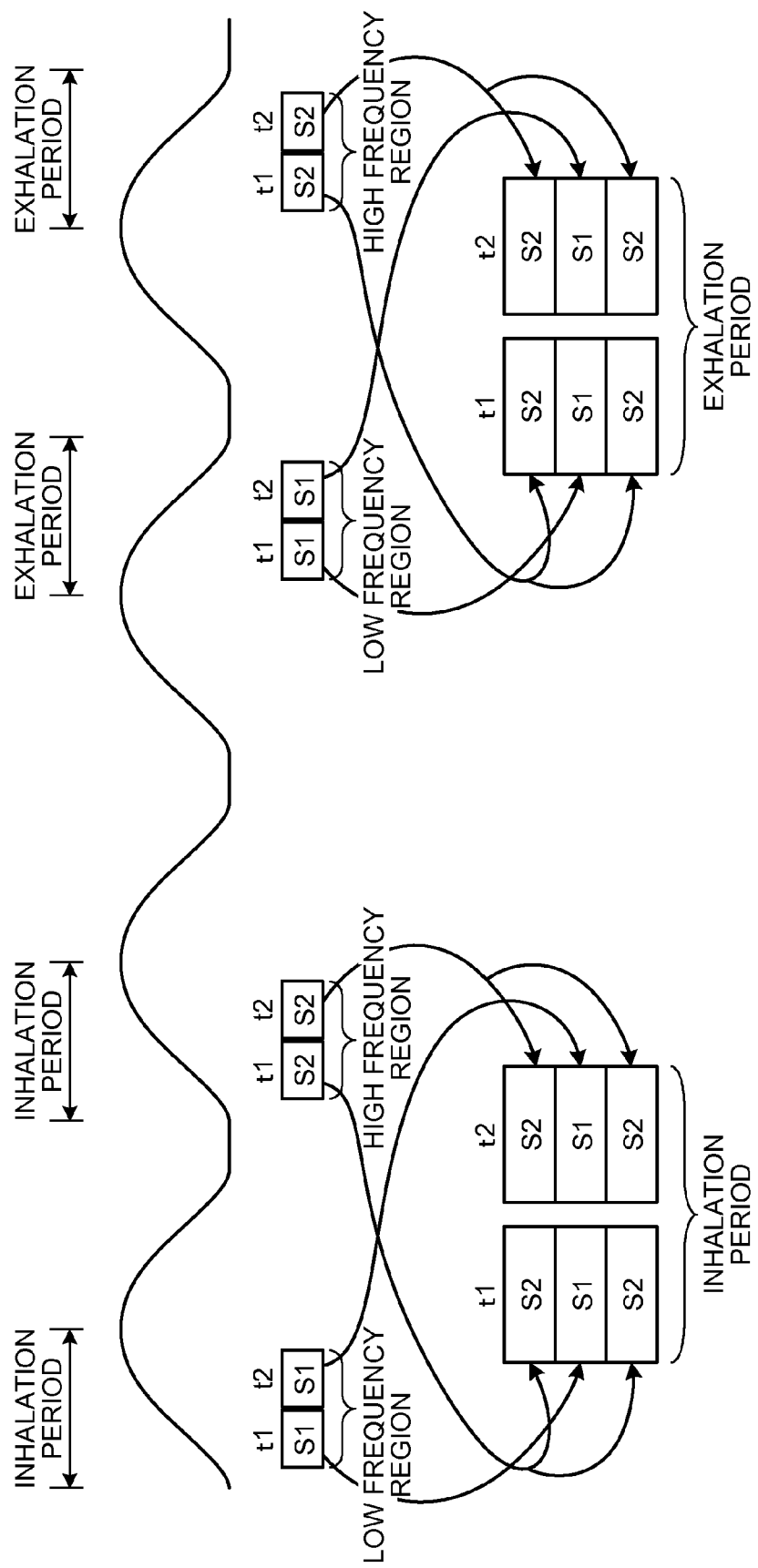
FIG. 11 is a diagram for explaining the relation between data collection and a segment in a second embodiment.

FIG. 11 is a diagram for explaining the relation between the data collection and the segment in the second embodiment. As illustrated in FIG. 11, for example, the data collection unit 26a collects data in a low frequency region of the k-space over a plurality of time phases within one respiratory cycle, and data in a high frequency region of the k-space over the time phases within one respiratory cycle. In this case, the CSF image generation unit 26b combines the data in the low frequency region and the data in the high frequency region to generate CSF images of the time phases. When combining the data in the low frequency region and the data in the high frequency region, the CSF image generation unit 26b may simply replicate the data, or may weight the data with the respiratory cycles.

The correlation between one respiratory cycle and another respiratory cycle can be low in some cases. This results in a low correlation between the pieces of data if they are of the same time phase but collected in different respiratory cycles. Consequently, one CSF image is generated by combining data of the segment 1 and the segment 2 that are not much correlated, which may result in averaging the data and hence impairing sufficient observation of the kinetics of the CSF in the desired respiratory cycle.

In a case where data of the segment 1 and data of the segment 2 are obtained separately in the low frequency region and the high frequency region, properties of pieces of information held by the data of respective segments are different. Thus, the influence on the CSF image may be reduced even when the correlation between the respiratory cycles is low. That is, the data in the low frequency region is the data in the vicinity of the center of the k-space, and information of a rough signal distribution and the contrast of the image is held in here. The data in the high frequency region holds another piece of information. As described above, the properties of the pieces of information held by the low frequency region and the high frequency region are different, which reduces the influence on the CSF image even with a low correlation between the respiratory cycles.

Figure 12A:
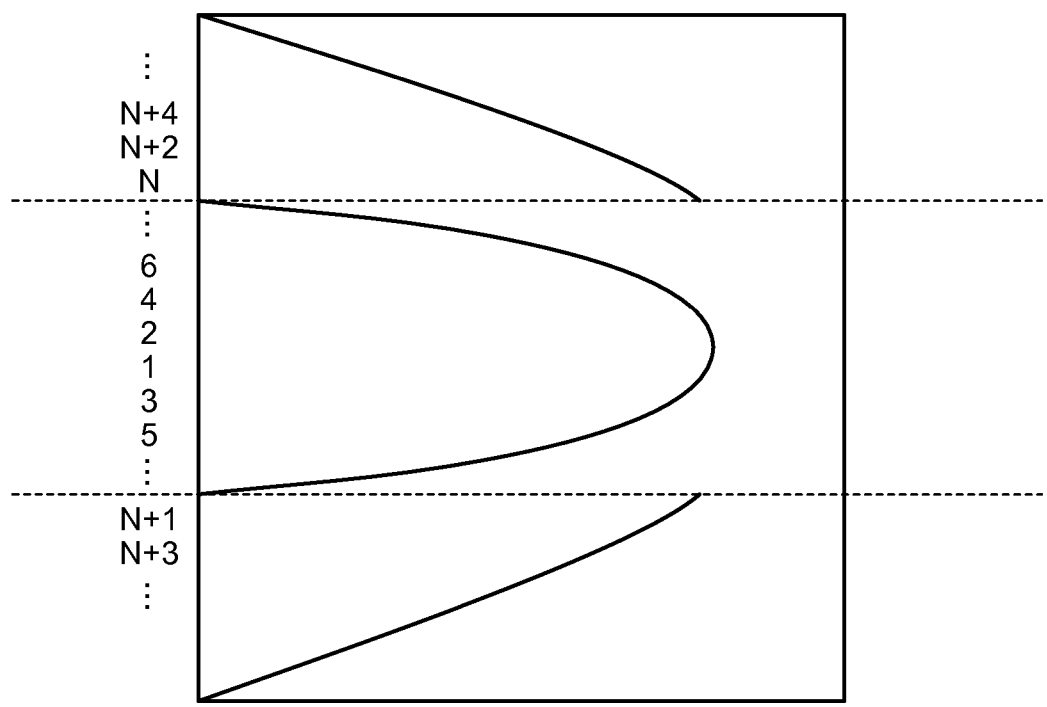
FIG. 12A is a diagram for explaining the data collection in the second embodiment.
Figure 12B:
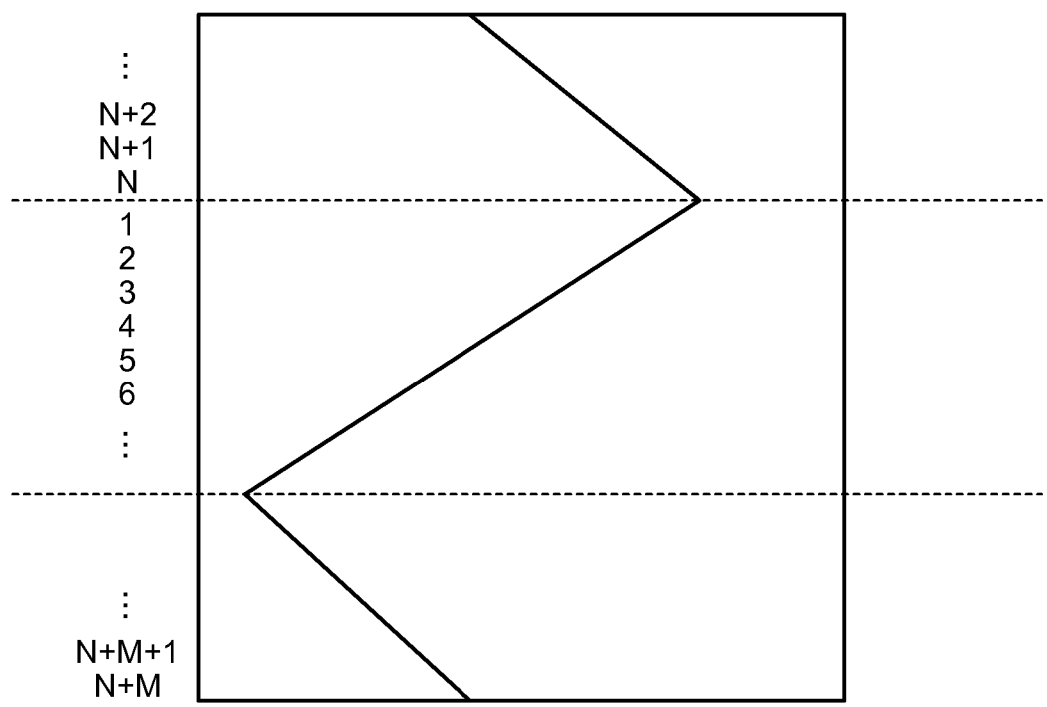
FIG. 12B is a diagram for explaining the data collection in the second embodiment.

FIG. 12A and FIG. 12B are diagrams for explaining the data collection in the second embodiment. FIG. 12A and FIG. 12B both illustrate the k-space, and the vertical direction thereof corresponds to the phase encoding direction. In FIG. 12A and FIG. 12B, a dotted line on the k-space denotes a boundary between the low frequency region and the high frequency region. In FIG. 12A and FIG. 12B, a solid line on the k-space denotes a signal value (higher in the right-hand direction).

For example, as illustrated in FIG. 12A, the data collection unit 26a according to the second embodiment collects the data in the low frequency region in a centric order from the center in the phase encoding direction (the order of "1", "2", "3" . . . in FIG. 12A) within a respiratory cycle. It can be seen that the signal value is high in an initial phase but gradually decreases. Subsequently, the data collection unit 26a collects the data in the high frequency regions within the next respiratory cycle in the order of "N", "N+1", "N+2" . . . from the boundaries with the low frequency region. It can also be seen that the signal value is high in the initial phase but gradually decreases.

In the case of FIG. 12A, the difference between the signal values is significantly large at the boundaries between the low frequency region and the high frequency region, which may result in generating artifacts in the image.

For example, as illustrated in FIG. 12B, the data collection unit 26a according to the second embodiment collects data in the low frequency region, within a certain respiratory cycle in a sequential order (the order of "1", "2", "3" . . . in FIG. 12B). It can also be seen that the signal value is high in the initial phase but gradually decreases. Subsequently, the data collection unit 26a collects data in the high frequency region within the next respiratory cycle in the order of "N", "N+1", "N+2" . . . , and then in the order of "N+M", "N+M+1", "N+M+2" . . . . It can also be seen that the signal value is high in the initial phase but gradually decreases.

In the case of FIG. 12B, the difference between the signal values is small at the boundaries between the low frequency region and the high frequency region, which reduces generation of artifacts in the image. However, this means that the signal value of the data at the center of the k-space is not so high. Thus, the CSF image generation unit 26b may preferably shift the position of the center of imaging by a particular amount when reconstructing the thus collected data of the k-space.

Modification of Second Embodiment

Figure 15:
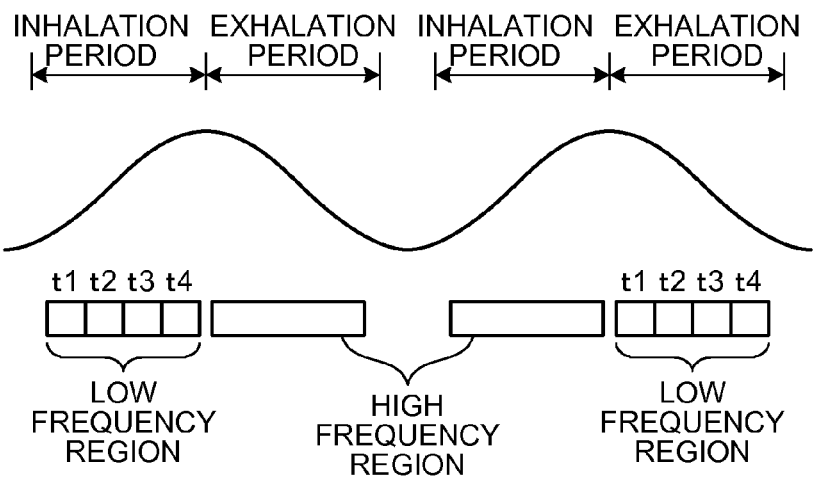
FIG. 15 is a diagram for explaining the data collection in the modification of the second embodiment.

Next, a modification of the second embodiment will be described. FIG. 13 to FIG. 15 are diagrams for explaining data collection in the modification of the second embodiment. As illustrated in FIG. 13 and FIG. 14, the data collection unit 26a according to the modification of the second embodiment collects data in the entire k-space (whole region) for one time phase within one respiratory cycle and data in part of the k-space (low frequency region) for a plurality of time phases within one respiratory cycle. In this case, the CSF image generation unit 26b combines the data in the high frequency region among the data in the entire k-space for one time phase with the data in the low frequency region for each of the time phases to generate the CSF images of the time phases.

That is, the data collection unit 26a firstly collects data in the entire k-space for one time phase because a larger amount of data can be collected if the collection is performed for one time phase. The data collection unit 26a then collects data in the low frequency region. In this case, the data volume decreases as compared to the case of the entire k-space, so that the collection can be performed for more time phases. As described above, because information of the rough signal distribution, the contrast of the image, and the like is held by the data in the low frequency region, data in the other regions may be used in common among all time phases as long as the data in the low frequency region is collected for each of the time phases. In this manner, the CSF image generation unit 26b combines the data in the high frequency region among the data of the entire k-space for one time phase with the data in the low frequency region for each of the time phases to generate the CSF images of the time phases. When combining the data in the high frequency region with the data in the low frequency region of each of the time phases, the CSF image generation unit 26b may simply replicate the data, or may weight the data with respiratory cycles.

As illustrated in FIG. 13, the data of the entire k-space (the data required for reconstructing the image: for example, the data of the entire k-space in a case of a typical reconstruction (full reconstruction); and the data of half or more of the k-space in a case of applying the half-Fourier method) may be collected for both the inhalation period and the exhalation period within one respiratory cycle. Alternatively, as illustrated in FIG. 14, the data of the entire k-space may be separately collected for the inhalation period and the exhalation period.

Alternatively, as illustrated in FIG. 15, the data collection unit 26a according to the modification of the second embodiment may collect data in the low frequency region of the k-space for a plurality of time phases within one respiratory cycle and data in the high frequency region of the k-space for one time phase within the same respiratory cycle. For example, as illustrated in FIG. 15, the data collection unit 26a firstly collects data in the low frequency region for a plurality of time phases in an inhalation period, and then collects data in the high frequency region for one time phase in the subsequent exhalation period. In the subsequent respiratory cycle, the data collection unit 26a firstly collects data in the high frequency region for one time phase in the inhalation period, and then collects data in the low frequency region for the time phases in the subsequent exhalation period.

In this case, for example, the CSF image generation unit 26b may preferably generate the CSF images of the time phases in the inhalation period by combining the data in the low frequency region for each of the time phases collected in the first respiratory cycle and the data in the high frequency region collected in the second respiratory cycle. Similarly, for example, the CSF image generation unit 26b may preferably generate the CSF images of the time phases in the exhalation period by combining the data in the low frequency region for each of the time phases collected in the second respiratory cycle and the data in the high frequency region collected in the first respiratory cycle.

Alternatively, for example, the data collection unit 26a may only perform data collection for one respiratory cycle, and the CSF image generation unit 26b may generate a CSF image by using only data for one respiratory cycle. For example, the CSF image generation unit 26b may combine data in the low frequency region for each of the time phases collected in a certain respiratory cycle with data in the high frequency region collected in the same respiratory cycle to generate the CSF images of the time phases. In this case, if data in the low frequency region is collected in the "inhalation period" within the respiratory cycle, the CSF image generation unit 26b generates the CSF images of the time phases for the "inhalation period".

Third Embodiment

Next, a third embodiment will be described. The above-described embodiments describe the examples in which the inversion pulse is applied with the starting of the inhalation period or the exhalation period as a trigger, and the data of the desired period (for example, the period in which the respiratory fluctuation is large, the period of exhalation, and the period of inhalation) in the respiratory cycle is selectively collected. However, the embodiments are not limited thereto. The MRI apparatus 100 according to the third embodiment may have the same configuration as that of the MRI apparatus 100 according to the other embodiments unless otherwise specifically noted.

In the third embodiment, the data collection unit 26a continuously collects data of an imaging area independently of the respiratory cycle of the subject P. At the same time, the data collection unit 26a also collects data indicating a time phase of a respiratory cycle. The CSF image generation unit 26b selectively generates CSF images of a plurality of time phases in a desired period by using the data of the imaging area continuously collected and the data indicating the time phase of the respiratory cycle.

Figure 16:
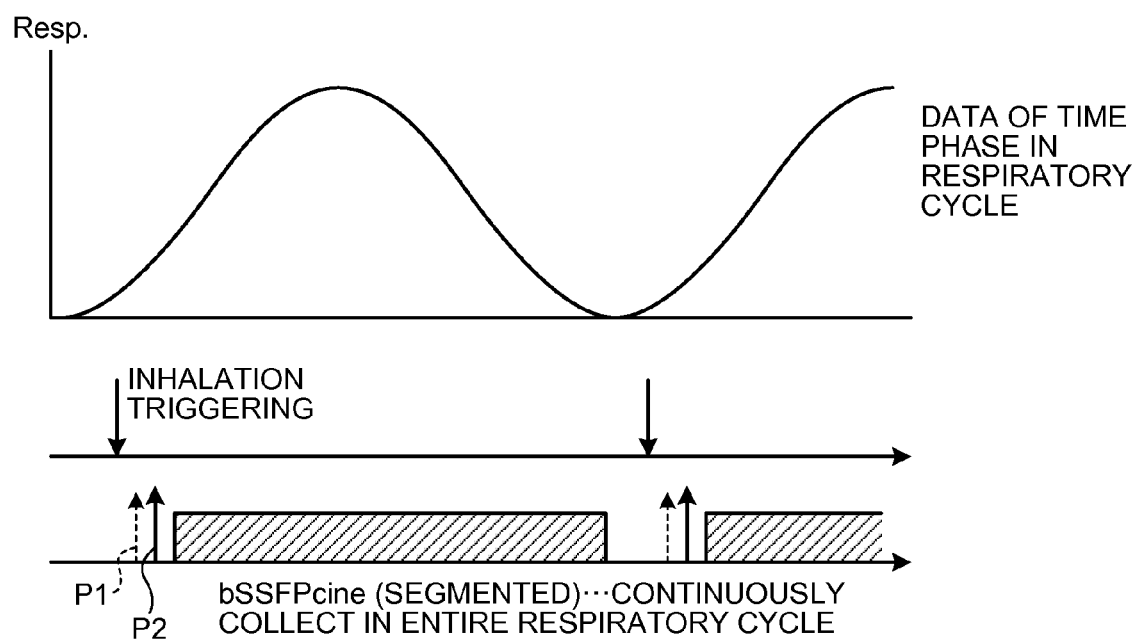
FIG. 16 is a diagram for explaining data collection in a third embodiment.

FIG. 16 is a diagram for explaining data collection in the third embodiment. For example, as illustrated in FIG. 16, the data collection unit 26a continuously collects the data of the imaging area for the entire respiratory cycle after applying an inversion pulse in synchronization with the starting of an inhalation. At the same time, the data collection unit 26a also collects the data indicating the time phase of the respiratory cycle such as a signal indicating detection of the fluctuation of the diaphragm of the subject or a signal indicating detection of the fluctuation of the marker fitted to the subject. Subsequently, on the basis of the data indicating the time phase of the respiratory cycle, the CSF image generation unit 26b extracts data of a plurality of time phases, for example, collected in an initial period in which the respiratory fluctuation is large in the period of inhalation, from the data continuously collected over the entire respiratory cycle. The CSF image generation unit 26b selectively generates CSF images in that period by using the extracted data.

The inversion pulse is not limited to one applied in synchronization with the starting of the inhalation, and may be applied in synchronization with the starting of an exhalation, for example. The CSF image in the desired period generated by the CSF image generation unit 26b is not limited to one in the period of inhalation, and may be generated in the period of exhalation or any other period, for example. Because the data indicating the time phase of the respiratory cycle is collected at the same time, the CSF image generation unit 26b may subsequently generate the CSF image of any period.

The third embodiment describes the example of synchronizing with the respiratory cycle as a trigger for applying the inversion pulse. However, in such a case too, the data collection is not performed in synchronization with the respiratory cycle but only performed continuously. The embodiments are not limited thereto. The trigger for applying the inversion pulse may be another biological signal such as an electrocardiographic signal or a pulse wave signal, a clock signal of the MRI apparatus 100, or the like.

Fourth Embodiment

Next, a fourth embodiment will be described. In the fourth embodiment, the number of segments is variable and adjusted depending on the period in a respiratory cycle. Specifically, the data collection unit 26a collects data of an imaging area by changing the number of segments and the time window width for data collection depending on the period in the respiratory cycle. The description in the fourth embodiment may be applied to a case where data in a desired period is selectively collected or a case where data is subsequently selected from the data collected for the entire respiratory cycle and a CSF image in a desired period is generated.

Figure 17:
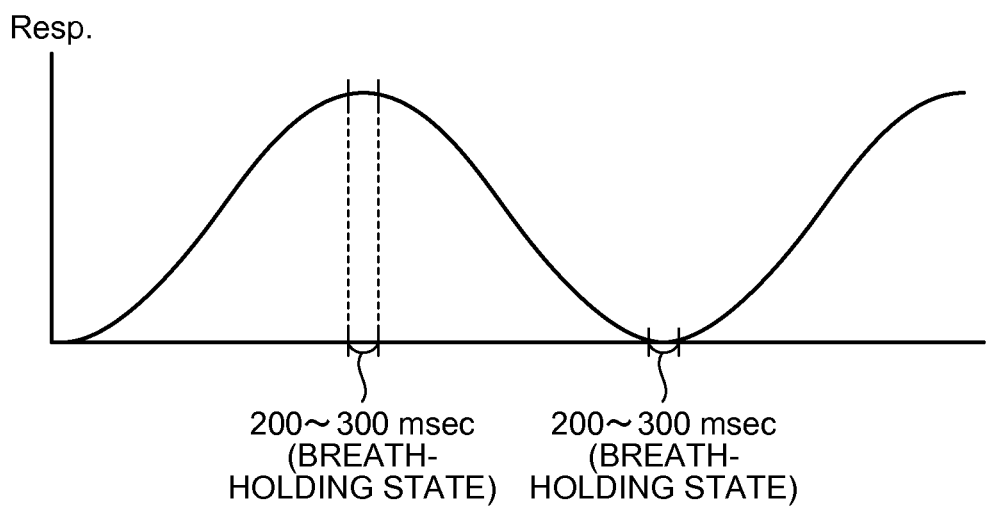
FIG. 17 is a diagram for explaining a transition period in a fourth embodiment.

FIG. 17 is a diagram for explaining a transition period between the exhalation and the inhalation in the fourth embodiment. As illustrated in FIG. 17, it is considered that there is a period in a state substantially similar to breath-holding (hereinafter, referred to as transition period as appropriate), which is a short period of about 200 to 300 milliseconds, between a period of exhalation and a period of inhalation.

Figure 18:
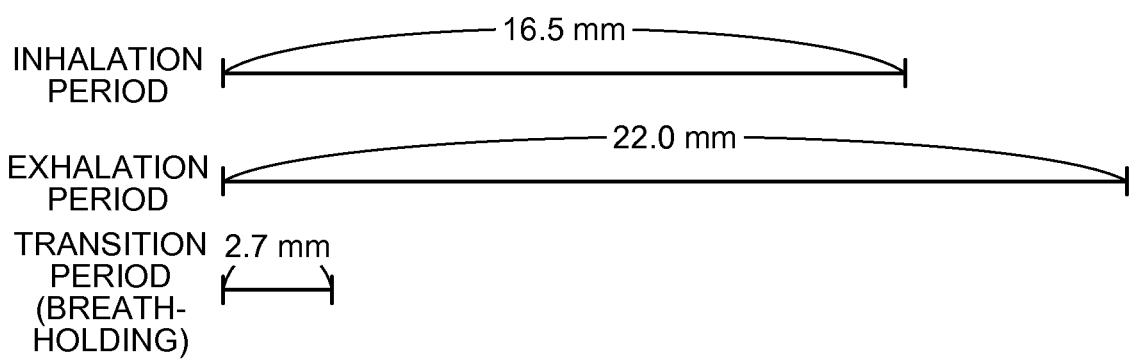
FIG. 18 is a diagram for explaining a displacement of CSF in each period in the fourth embodiment.

FIG. 18 is a diagram for explaining a displacement of the CSF in each of the periods in the fourth embodiment. FIG. 18 illustrates examples of the displacement of the CSF measured in the period of inhalation, the period of exhalation, and the transition period thereof. For example, the CSF moves 16.5 millimeters in the period of inhalation and moves 22.0 millimeters in the period of inhalation, while it moves only 2.7 millimeters in the transition period. In this manner, the CSF moves in the period of inhalation or exhalation, about eight to ten times larger than in the transition period. The movement in the period of inhalation or exhalation is a momentary movement in a very short time in many cases.

Figure 19A:
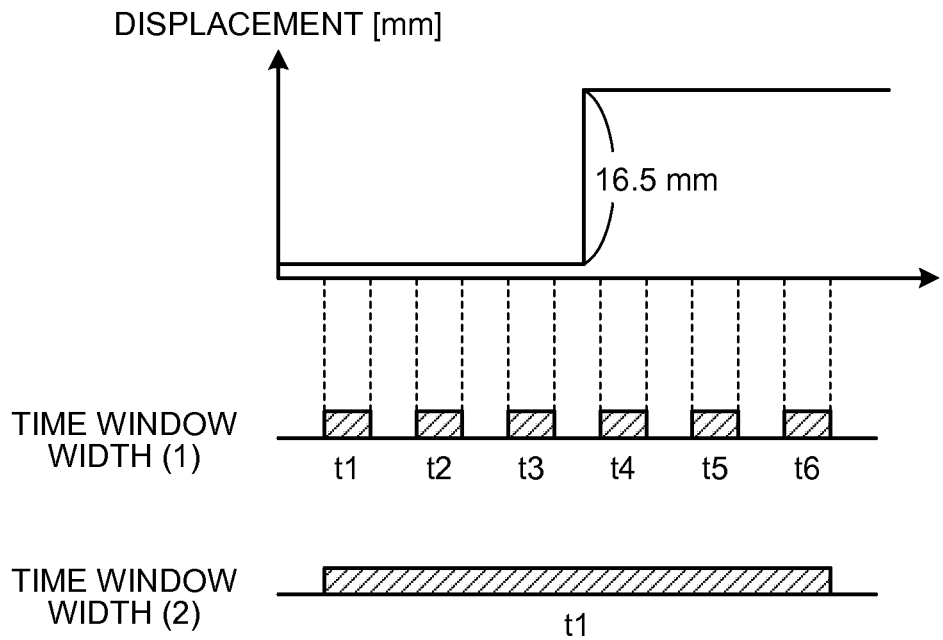
FIG. 19A is a diagram for explaining the relation between the displacement of the CSF and a time window width of data collection in the fourth embodiment.
Figure 19B:
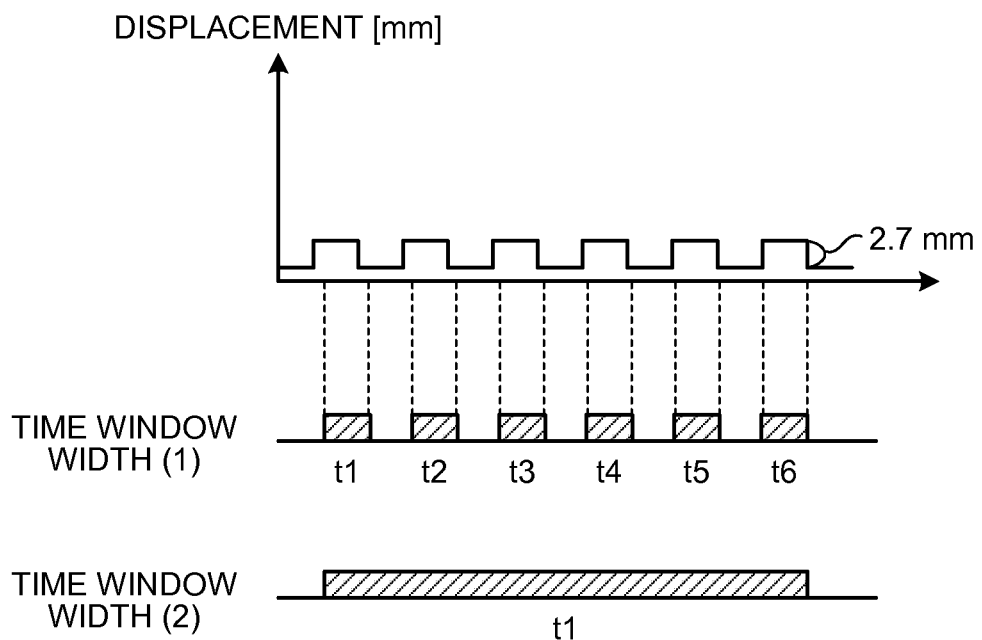
FIG. 19B is a diagram for explaining the relation between the displacement of the CSF and the time window width of the data collection in the fourth embodiment.

FIG. 19A and FIG. 19B are diagrams for explaining the relation between the displacement of the CSF and the time window width of the data collection in the fourth embodiment. For example, as illustrated in FIG. 19A, it is assumed that the CSF moves 16.5 millimeters in a very short time in the period of inhalation or exhalation. If the data collection unit 26a increases the number of segments, reduces the data collection size, and collects data of a plurality of time phases while shortening the time window width as illustrated with the time window width (1), the kinetics of the CSF may not be captured when the movement of the CSF occurs between the windows. For example, in the example of FIG. 19A, the movement of the CSF occurs between windows of a time phase t3 and a time phase t4, and the movement of the CSF is not captured in any data. If the data collection unit 26a reduces the number of segments, increases the data collection size, and collects the data of a single time phase while widening the time window width as illustrated with the time window width (2), the movement of the CSF occurred between the windows of the time phase t3 and the time phase t4 can be captured.

For example, as illustrated in FIG. 19B, it is assumed that the CSF moves gradually with the displacement of about 2.7 millimeters in the period of inhalation or exhalation. If the data collection unit 26a increases the number of segments, reduces the data collection size, and collects the data of a plurality of time phases while shortening the time window width as illustrated with the time window width (1), the gradual movement of the CSF can be captured. In contrast, if the data collection unit 26a reduces the number of segments, increases the data collection size, and collects the data of a single time phase while widening the time window width as illustrated with the time window width (2), the gradual movement of the CSF cannot be captured.

Therefore, in the fourth embodiment, the data collection unit 26a reduces the number of segments in the period of exhalation and the period of inhalation within one respiratory cycle and collects data having a relatively large data collection size with a relatively long time window width. In contrast, the data collection unit 26a increases the number of segments in the transition period between the exhalation and the inhalation and collects data having a relatively small data collection size with a relatively short time window width.

FIG. 20 is a diagram for explaining the data collection in the fourth embodiment. For example, the data collection unit 26a collects data for one image with a time window width of 200 to 300 milliseconds in the period of exhalation and the period of inhalation. In contrast, for example, the data collection unit 26a collects data having a size of, for example, one image divided into 8 or 16 pieces with a time window width of 30 to 40 milliseconds in the transition period.

In the example illustrated in FIG. 20, the data for one image is collected in the period of exhalation and the period of inhalation, so that data of each time phase collected in this period completes the collection of the data for one image within one respiratory cycle. In contrast, only a piece of data such as one having a size of one image divided into 8 or 16 pieces is collected in the transition period. Thus, typically, the collection of the data for one image is completed through repetition over 8 respiratory cycles or 16 respiratory cycles. The numerical values described herein are merely an example and may be optionally changed according to an imaging form and the like.

The imaging condition derivation unit 26c may prepare a graphical user interface (GUI) as appropriate for adjusting the number of segments and display the GUI on the display unit 25. For example, after detection of the respiratory fluctuation illustrated in FIG. 6, the imaging condition derivation unit 26c displays the waveform of the respiratory fluctuation on the display unit 25 and receives an input of the number of segments corresponding to each of the periods from the operator. The imaging condition derivation unit 26c then derives the number of time phases collectable during each of the periods from the input number of segments and a predetermined time window width for each of the periods. Alternatively, for example, the imaging condition derivation unit 26c receives the input of the number of time phases corresponding to each of the periods. The imaging condition derivation unit 26c then derives the number of time segments during each of the periods from the input number of time phases and the predetermined time window width for each of the periods.

As described above, according to the fourth embodiment, the data of the imaging area is collected by adjusting the data collection size and the time window width as variables depending on the period in the respiratory cycle, so that the kinetics of the CSF that is different depending on the period can be completely captured. In a case where the CSF image generated from the data thus collected is displayed as a moving image, the kinetics of the CSF can be observed in more natural movement.

As illustrated in FIG. 19A, in the fourth embodiment described above, when the time window width is shortened and the movement of the CSF occurs between the time phases (between the windows), it is considered that the movement thereof may not be captured. Such an overlooking can be prevented if the intervals between the time phases (the intervals between the windows) can be reduced as much as possible, for example.

For example, when the time window width is relatively short and the intervals between the windows are kept as small as possible, the data collection unit 26a collects the data of the entire respiratory cycle with this time window width and the size of the segment corresponding thereto. In this case, subsequently, the CSF image generation unit 26b may preferably generate the CSF images of the time phases while adjusting the data volume used for generating one CSF image as appropriate.

For example, the CSF image generation unit 26b may preferably bring together the pieces of data collected with a plurality of time window widths to generate one CSF image for the period of exhalation and the period of inhalation. For the transition period, for example, the CSF image generation unit 26b may preferably use the data collected with one time window width to generate one CSF image.

Fifth Embodiment

Next, a fifth embodiment will be described. In the fifth embodiment, an inversion pulse is inserted between segments. Specifically, to collect, over a plurality of time phases within one respiratory cycle, a piece of data for one segment (or some pieces of data among data of the k-space divided into a plurality of segments) among data of an imaging area divided into a plurality of segments, the data collection unit 26a inserts and applies the inversion pulse between pieces of data of different time phases.

As described above, a respiratory cycle is 8 seconds for example, but a period in which contrast is provided to the image by applying the inversion pulse is about 4 seconds or less, for example. Thus, in the fifth embodiment, the data collection unit 26a inserts the inversion pulses as appropriate so as to continuously provide contrast. This may leave a plurality of labeling marks on the imaged CSF, but is effective in light of maintenance of contrast.

FIG. 21 and FIG. 22 are diagrams for explaining the application of the inversion pulse in the fifth embodiment. For example, as illustrated in (A) of FIG. 21, the data collection unit 26a typically applies an inversion pulse with the starting of an inhalation as a trigger, and thereafter continuously collects the data for one segment over a plurality of time phases.

In contrast, as illustrated in (B) of FIG. 21, for example, the data collection unit 26a according to the fifth embodiment applies an inversion pulse with the starting of the inhalation as a trigger, and thereafter collects the data for one segment for one time phase. Subsequently, the data collection unit 26a applies an inversion pulse again and collects the data for the same segment for one time phase. In this manner, the data collection unit 26a according to the fifth embodiment inserts and applies the inversion pulses between pieces of data of different time phases.

Similarly, as illustrated in (A) of FIG. 22, for example, the data collection unit 26a typically applies an inversion pulse with the starting of an inhalation as a trigger, and thereafter collects data of the entire k-space. Subsequently, the data collection unit 26a applies an inversion pulse with the starting of an inhalation as a trigger, and continuously collects data in a low frequency region over a plurality of time phases.

As illustrated in (B) of FIG. 22, for example, the data collection unit 26a according to the fifth embodiment applies an inversion pulse with the starting of an inhalation as a trigger, and thereafter collects the data of the entire k-space. Subsequently, the data collection unit 26a applies an inversion pulse with the starting of an inhalation as a trigger, and collects data in the low frequency region for one time phase. Subsequently, the data collection unit 26a collects the data in the low frequency region for a plurality of time phases while applying inversion pulses between time phases.

The embodiment is not necessarily limited to inserting the inversion pulses between all of the time phases. For example, the data collection unit 26a may insert the inversion pulses every two or three time phases. Timing for inserting the inversion pulse is typically determined in advance by options such as "every two time phases" and "every 100 milliseconds" at the setting of the imaging conditions or the like.

Other Embodiments

The embodiments are not limited to those described above. For example, the embodiments may be modified as described below.

The embodiments above describe an example in which data is collected in both of the inhalation period and the exhalation period. However, the embodiment is not limited thereto, and data may be collected only in the inhalation period or in the exhalation period. When the collected data is used for physiological purposes, it is typically preferable to collect data in both of the inhalation period and the exhalation period. However, when the collected data is used for clinical purposes, it may be sufficient to collect data in one of the periods.

The embodiments above describe an example in which the data of the k-space is divided into a plurality of segments, but are not limited thereto. The data collection unit 26a may collect the whole data for reconstructing one image as one segment over a plurality of time phases within one respiratory cycle. The embodiments above describe the example of two segments or two time phases, but are not limited thereto. The number of segments and the number of time phases may be optionally changed.

The embodiments above mainly describe an example in which data of a plurality of time phases is collected for a certain segment in a certain respiratory cycle when the data of the k-space is divided into a plurality of segments, but the embodiments are not limited thereto. For example, the data collection unit 26a collects data of single phase encode line or a plurality of phase encode lines included in each of the divided segments from all of the segments in a certain respiratory cycle. The data collection unit 26a performs this collection of the data of single or a plurality of phase encode lines from all of the segments over a plurality of time phases in a certain respiratory cycle. The data collection unit 26a repeats this collection over a plurality of respiratory cycles while changing the phase encode line to be collected, so as to collect the data corresponding to one image for a plurality of time phases.

The embodiments above describe an example in which the non-selective inversion pulse and the selective inversion pulse are applied, but the embodiments are not limited thereto. For example, the data collection unit 26a may apply the inversion pulse by using the pulsed continuous arterial spin labeling (pCASL) method for continuously radiating the inversion pulse. The data collection unit 26a may collect two kinds of CSF images by alternately repeating, for every respiratory cycle, the collection in which the labeling is performed by the inversion pulse and the collection in which the labeling is not performed. The CSF image generation unit 26b generates a difference image of the two kinds of CSF images in the same time phase, so that only a labeled portion is extracted and a background signal is reduced.

The embodiments above describe an example in which whole data for a desired time phase is collected within one respiratory cycle, but the embodiments are not limited thereto. For example, when not the whole data for a desired time phase can be collected within one respiratory cycle due to the data volume of one segment, the data collection unit 26a may collect the data for the desired time phase in a distributed manner over a plurality of respiratory cycles.

According to the magnetic resonance imaging apparatus and the method for magnetic resonance imaging of at least one of the above-described embodiments, the kinetics of the cerebrospinal fluid can be appropriately visualized.

While certain embodiments have been described, these embodiments have been presented by way of example only, and are not intended to limit the scope of the inventions. Indeed, the novel devices and methods described herein may be embodied in a variety of other forms; furthermore, various omissions, substitutions and changes in the form of the devices and methods described herein may be made without departing from the spirit of the inventions. The accompanying claims and their equivalents are intended to cover such forms or modifications as would fall within the scope and spirits of the inventions. For example, parallel imaging may be combined with the MR imaging according to the embodiment. In this case, a plurality of reception coils are used as the reception coil 8 described above. That is, the parallel imaging is a method for performing high-speed imaging by using a plurality of reception coils for imaging and utilizing difference in sensitivities of respective reception coils, and typically includes a sensitivity encoding (SENSE) system and a simultaneous acquisition of spatial harmonics (SMASH) system. The SENSE system performs processing on Fourier-transformed image data, and the SMASH system performs processing on data of the k-space before Fourier transformation. In the embodiments above, the cerebrospinal fluid (CSF) is described as an imaging target. However, the embodiments may be applied to pancreatic juice or lymph fluid. That is, it is clinically useful to apply the embodiments to fluid of which correlation with a cardiac phase is low, such as pancreatic juice or lymph fluid, not limited to the CSF, except fluid of which correlation with a cardiac phase is high, such as blood.

What is claimed is:

1. A magnetic resonance imaging apparatus comprising:
a collection circuitry configured to collect data of an imaging area over a plurality of time phases in a certain respiratory cycle after applying a labeling pulse to a labeling area in which cerebrospinal fluid flows under a task of respiration, wherein the labeling pulse is applied in synchronization with a signal of instruction given to a subject; and
a generation circuitry configured to generate images of a plurality of time phases depicting the cerebrospinal fluid by using collected data.

2. The magnetic resonance imaging apparatus according to claim 1, wherein the collection circuitry collects the data of the imaging area during a period in which respiratory fluctuation is large in the respiratory cycle.

3. The magnetic resonance imaging apparatus according to claim 1, wherein
the collection circuitry collects part of the data of the imaging area divided into a plurality of segments over a plurality of time phases within one respiratory cycle; and
the generation circuitry generates the images of the time phases by combining pieces of data collected in respective respiratory cycles.

4. The magnetic resonance imaging apparatus according to claim 1, further comprising a derivation circuitry configured to specify a period in which respiratory fluctuation is large based on a waveform of the respiratory fluctuation of a subject, and derives at least one of the number of segments and the number of time phases as an imaging condition for collecting the data according to the specified period, wherein
the collection circuitry collects the data of the imaging area according to the derived imaging condition.

5. The magnetic resonance imaging apparatus according to claim 1, further comprising a display controller circuitry configured to display, in parallel or as a moving image, the generated images of the time phases on a display.

6. The magnetic resonance imaging apparatus according to claim 1, wherein
the collection circuitry collects the data of the imaging area over the time phases during a certain period in the respiratory cycle, and
the generation circuitry generates the images of the time phases depicting the cerebrospinal fluid in the certain period.

7. The magnetic resonance imaging apparatus according to claim 1, wherein
the collection circuitry collects the data of the imaging area over the time phases in at least one of a period in which respiratory fluctuation is large, a period of exhalation, and a period of inhalation, and
the generation circuitry generates the images of the time phases depicting the cerebrospinal fluid in at least one of the period in which the respiratory fluctuation is large, the period of exhalation, and the period of inhalation.

8. A magnetic resonance imaging apparatus comprising:
a collection circuitry configured to collect data of an imaging area over a plurality of time phases within a certain respiratory cycle after applying a labeling pulse to a labeling area in which cerebrospinal fluid flows under a task of respiration, wherein the labeling pulse is applied in synchronization with a signal of instruction given to a subject; and a generation circuitry configured to generate images of a plurality of time phases depicting the cerebrospinal fluid during a certain period specified based on a waveform of a respiratory fluctuation in the respiratory cycle by using the collected data.

9. The magnetic resonance imaging apparatus according to claim 8, wherein the collection circuitry selectively collects data during a certain period in the respiratory cycle; and the generation circuitry generates the images of a plurality of time phases during the certain period by using the selectively collected data.

10. The magnetic resonance imaging apparatus according to claim 8, wherein the collection circuitry selectively collects data in at least one of a period in which respiratory fluctuation is large, a period of exhalation, and a period of inhalation in the respiratory cycle; and the generation circuitry generates the images of a plurality of time phases in at least one of the period in which the respiratory fluctuation is large, the period of exhalation, and the period of inhalation.

11. The magnetic resonance imaging apparatus according to claim 8, further comprising a display controller circuitry configured to display, in parallel or as a moving image, the images of the time phases depicting the cerebrospinal fluid during a certain period in the respiratory cycle, on a display.

12. A method for magnetic resonance imaging executed by a magnetic resonance imaging apparatus, the method comprising:

collecting data of an imaging area over a plurality of time phases in a certain respiratory cycle after applying a labeling pulse to fluid of which correlation with a cardiac phase is low under a task of respiration, wherein the labeling pulse is applied in synchronization with a signal of instruction given to a subject; and generating images of a plurality of time phases indicating kinetics of the fluid by using the collected data.

\* \* \* \* \*